United States Patent [19]

Hu et al.

[11] Patent Number: 5,583,221

[45] Date of Patent: Dec. 10, 1996

[54] SUBSTITUTED FUSED AND BRIDGED BICYCLIC COMPOUNDS AS THERAPEUTIC AGENTS

[75] Inventors: Hong Hu, Chapel Hill; G. Erik Jagdmann, Jr., Apex; Jose S. Mendoza, Durham, all of N.C.

[73] Assignee: Eli Lilly and Company, Indianapolis, Ind.

[21] Appl. No.: 392,710

[22] Filed: Feb. 23, 1995

Related U.S. Application Data

[63] Continuation-in-part of Ser. No. 237,645, May 4, 1994, abandoned.

[51] Int. Cl.$^6$ .................. C07D 487/00; C07C 69/76; A01N 43/46; A01N 37/10
[52] U.S. Cl. .................. 540/520; 549/369; 560/52; 560/56; 562/460
[58] Field of Search .................. 540/520; 560/52, 560/56; 514/214, 533, 568; 562/460; 549/369

[56] References Cited

FOREIGN PATENT DOCUMENTS

WO93/03730  3/1993  WIPO.
WO94/20062  9/1994  WIPO.

OTHER PUBLICATIONS

CA122:81925 1994.
CA121:300627 1994.
CA121:280445 1994.
CA119:249745 1993.
Kikkawa, et al., "Rapid Purificatiion of Protein Kinase C by High Performance Liquid Chromatography", *Biochem. Biophys. Res. Comm.*, 1986, 135, 636.

McArdle, et al., "Use of Protein Kinase C–Depleted Cells for Investigation of the Role of Protein Kinase C in Stimulus–Response Coupling in the Pituitary", Methods *Enzym.*, 1989, 168, 287.

Osada, et al., "Rapid Screening Method for Inhibitors of Protein Kinase C", *J. Antibiotics*, 1988, 41, 547.

Mendoza et al., "Synthesis and Biological Evaluation of Conformationally Constrained Bicyclic Balanol Analogues as Inhibitors of Protein Kinase C" Presented to the Washington D.C. ACS Meeting, Aug. 21, 1994.

Atini, D., et al., *Amides and Amines with Analgesic and Antiniflammatory Activity*, 1971, 21(1), 30–6.

*Primary Examiner*—Paul J. Killos
*Attorney, Agent, or Firm*—James P. Leeds; Martin A. Hay; David E. Boone

[57] ABSTRACT

Compounds having the formula

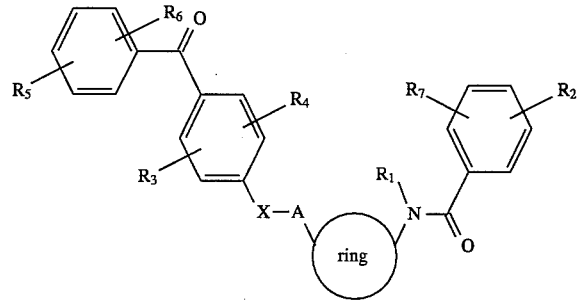

methods for using such compounds to inhibit protein kinase C in animals, including man are useful as inhibitors of protein kinase C. Also disclosed are pharmaceutical compositions including such compounds and compounds having the formula.

8 Claims, No Drawings

SUBSTITUTED FUSED AND BRIDGED BICYCLIC COMPOUNDS AS THERAPEUTIC AGENTS

This application is a continuation-in-part of U.S. application Ser. No. 08/237,645 filed on May 4, 1994, abandoned.

FIELD OF THE INVENTION

The present invention relates to treatments for inflammatory, cardiovascular, metabolic, nervous system, viral infectious, neoplastic, and other diseases. The present invention provides compounds which can inhibit protein kinase C isozymes (PKC). The present invention also provides compounds useful for treating inflammatory, cardiovascular, metabolic, nervous system, viral infectious, fungal infectious, neoplastic, and other diseases; compositions and methods useful in treating such diseases; and methods for preparing such compounds.

BACKGROUND OF THE INVENTION

Inhibition of PKC presently is believed to be one of the biochemical mechanisms by which the invented compounds produce their therapeutic effects. PKC is a family of calcium- and phospholipid-dependent serine/threonine-specific protein kinases which play an important role in cellular growth control, regulation, and differentiation. Activation of PKC has been implicated in several human disease processes including neoplasms. For example, cells transformed with the oncogenes ras,sis, erbB, abl, and src have been shown to contain elevated levels of diacylglycerol (DAG) which is believed to activate PKC. Additionally, several studies have shown increased expression of PKC in certain tumor types such as breast and lung carcinomas and activated PKC has been detected in human colon carcinomas. Further, PKC inhibitors have been reported to potentiate the antitumor activity of various chemotherapeutic agents including cis-platinum and doxorubicin.

Other human diseases in which PKC activation has been implicated include inflammatory diseases and reperfusion injury. PKC inhibitors have been demonstrated to block platelet aggregation and release of neutrophil activating agents such as platelet activating factor. PKC inhibitors also have been shown to inhibit neutrophil activation and chemotactic migration as well as neutrophil degranulation and release of proteolytic enzymes and reactive oxygen intermediates. Thus PKC inhibitors have the potential to block the most significant mechanisms of pathogenesis associated with inflammation and reperfusion injury.

SUMMARY OF THE INVENTION

The present invention resides in the discovery that substituted fused or bridged bicyclic ring compounds of Formula I, below, are useful in treating inflammatory, cardiovascular, metabolic, nervous system, viral infectious, fungal infectious, neoplastic, and other diseases. Formula I compounds inhibit PKC and inhibition of PKC is believed to be a biochemical mechanism of action of these compounds.

Presently preferred compounds of the invention include:

anti-3-[4-(2-Carboxy-6-hydroxybenzoyl)-3,5-dihydroxybenzoyloxy]-2-(4-hydroxybenzamido)-8-methyl-8-azabicyclo[3.2.1]octane;

syn-3-[4-(2-Carboxy-6-hydroxybenzoyl)-3,5-dihydroxybenzoyloxy]-2-(4-hydroxybenzamido)-8-methyl-8-azabicyclo[3.2.1]octane;

anti-2-(4-Hydroxybenzamido)-3-[4-(2-methoxycarbonyl-6-hydroxybenzoyl)-3,5-dihydroxybenzoyloxy]-8-methyl-8-azabicyclo[3.2.1]octane;

syn-2-[4-(2-Methoxycarbonyl-6-hydroxybenzoyl)-3,5-dihydroxybenzoyloxy]-3-(4-hydroxybenzamido)bicyclo[2.2.1]heptane;

syn-2-[4-(2-Carboxy-6-hydroxybenzoyl)-3,5-dihydroxybenzoyloxy]-3-(4-hydroxybenzamido)bicyclo[2.2.1]heptane;

anti-2-[4-(2-Carboxy-6-hydroxybenzoyl)-3,5-dihydroxybenzoyloxy]-3-(4-hydroxybenzamido)bicyclo[2.2.1]heptane;

anti-2-[4-(2-Methoxycarbonyl-6-hydroxybenzoyl)-3,5-dihydroxybenzoyloxy]-3-(4-hydroxybenzamido)bicyclo[2.2.1]heptane;

7-[4-(2-Methoxycarbonyl-6-hydroxybenzoyl)-3,5-dihydroxybenzoyloxy]-2-(hydroxybenzamido)bicyclo[2.2.1]heptane;

7-[4-(2-Carboxy-6-hydroxybenzoyl)-3,5-dihydroxybenzoyloxy]-2-(hydroxybenzamido)bicyclo[2.2.1]heptane;

syn-4-[4-(2-Carboxy-6-hydroxybenzoyl)-3,5-dihydroxybenzoyloxy]-3-(4-hydroxybenzoylamino)-1-azabicyclo[3.2.2]nonane;

anti-4-[4-(2-Carboxy-6-hydroxybenzoyl)-3,5-dihydroxybenzoyloxy]-3-(4-hydroxybenzoylamino)-1-azabicyclo[3.2.2]nonane;

anti-4-[4-(2-Methoxycarbonyl-6-hydroxybenzoyl)-3,5-dihydroxybenzoyloxy]-3-(4-hydroxybenzamido)-1-azabicyclo[3.2.2]nonane;

anti-1-(4-Hydroxybenzamido)-2-[3,5-dihydroxy-4-(2-carboxy-6-hydroxybenzoyl)benzoyloxy]indane;

syn-1-(4-Hydroxybenzamido)-2-[3,5-dihydroxy-4-(2-carboxy-6-hydroxybenzoyl)benzoyloxy]indane;

anti-1-(4-Hydroxybenzamido)-2-[3,5-dihydroxy-2-(2-hydroxy-6-methoxycarbonylbenzoyl)benzoyloxy]indane;

anti-1-[4-(2-Carboxy-6-hydroxybenzoyl)-3,5-dihydroxybenzyloxy]-2-(4-hydroxybenzamido)indane;

anti-2-[4-(2-Carboxy-6-hydroxybenzoyl)-3,5-dihydroxybenzoyloxy]-3-(4-hydroxybenzamido)bicyclo[2.2.1]-1,7,7-trimethylheptane;

8-exo-[4-(2-Carboxy-6-hydroxybenzoyl)-3,5-dihydroxybenzoyloxy]-9-endo-(4-hydroxybenzamido)tricyclo[5.2.1.0 (2.6)]decane;

8-endo-[4-(2-Carboxy-6-hydroxybenzoyl)-3,5-dihydroxybenzoyloxy]-9-endo-(4-hydroxybenzamido)tricyclo[5.2.1.0 (2.6)]decane;

(+)-anti-1-(4-Hydroxybenzamido)-2-[3,5-dihydroxy-4-(2-carboxy-6-hydroxybenzoyl)benzoyloxy]indane; and (−)-anti-1-(4-Hydroxybenzamido)-2-[3,5-dihydroxy-4-(2-carboxy-6-hydroxybenzoyl)benzoyloxy]indane.

The invention also includes a method for inhibiting PKC activity in mammals, including humans, which comprises administering to a subject an effective amount of one or more of the presently invented Formula I compounds. Included in the present invention are pharmaceutical compositions comprising compounds useful in the invented method and a pharmaceutical carrier.

Also included in the present invention are intermediates useful in preparing the invented Formula I compounds.

DETAILED DESCRIPTION OF THE INVENTION

The presently invented compounds that are pharmaceutically useful have the following formula:

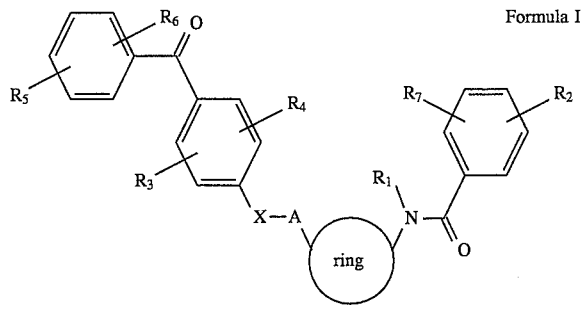

Formula I wherein:

is a fused or bridged bicyclic ring which includes (contains) 7–12 carbon atoms and may include (contain) one or more heteroatoms selected from the group of N, O and S;

X is

or $CH_2$;

A is O or $NR_8$;

$R_1$ and $R_8$ independently are H or lower alkyl;

$R_2$, $R_3$, $R_4$, $R_5$, $R_6$, and $R_7$ (when present) are any accessible combination of (are selected independently from) hydroxy, $C_{1-6}$ alkoxy, $C_{1-6}$ alkoxycarbonyl, carboxy, $C_{1-6}$ acyloxy, carboxamide, formyl, $C_{1-6}$ alkyl, halo, $CF_3$, amino, $C_{1-6}$ alkylamino, arylamino, $C_{1-6}$ alkylsulfonyl, $C_{1-6}$ alkylthio and $C_{1-6}$ alkylsulfinyl; and pharmaceutically acceptable salts thereof.

Preferred compounds of Formula I are compounds wherein

is a fused or bridged bicyclic ring which includes (contains) 7–9 carbon atoms and 0–1 nitrogen atoms, as the only heteroatoms;

A is O or NH;

$R_2$ to $R_6$ are a combination of (are selected independently from) hydroxy, carboxy, $C_{1-6}$ acyloxy, $C_{1-6}$ alkoxy, and $C_{1-6}$ alkoxycarbonyl; and $R_7$ is absent (is hydrogen).

As used in Formula I and elsewhere in this specification and claims "$C_{x-y}$ alkyl" and variations thereof are a straight chain or branched, saturated or unsaturated alkyl group containing x to y carbon atoms wherein x and y are integers and "halo" includes bromo, chloro, fluoro, and iodo. Some of the compounds included in Formula I can exist in more than one chiral form and thus exhibit stereoisomers. Formula I includes all purified stereoisomers and racemic mixtures of the compounds within its scope.

Examples of values for

are indan-1,2-diyl; 1-azabicyclo[3.2.2]nonan-3,4-diyl; 8-methyl-8-azabicyclo[3,2,1]octan-2,3-diyl; bicyclo [2.2.1] heptan-2,3-diyl; bicyclo[2.2.1]heptan-2,7-diyl; 1,7,7-trimethylbicyclo[2.2.1]heptan-2,3-diyl and tricyclo[5.2.1.0 (2,6)]decan-8,9-diyl.

Examples of values for $R_8$ when it represents a lower alkyl group are $C_{1-4}$ alkyl groups such as methyl.

Examples of values for $R_2$, $R_3$, $R_4$, $R_5$, $R_6$ or $R_7$ (when not hydrogen) are:

hydroxy;

for $C_{1-6}$ alkoxy: methoxy or ethoxy;

for $C_{1-6}$ alkoxycarbonyl: methoxycarbonyl or ethoxycarbonyl;

carboxy;

carboxamide;

formyl;

for $C_{1-6}$ alkyl: methyl or ethyl;

for halo: bromo, chloro or fluoro;

$CF_3$;

amino, for $C_{1-6}$ alkylamino: methylamino;

for arylamino: phenylamino;

for $C_{1-6}$ alkylsulfonyl: methanesulfonyl;

for $C_{1-6}$ alkylthio: methylthio; and for $C_{1-6}$ alkylsufinyl: methylsulfinyl.

$R_1$ preferably represents hydrogen.

Preferably $R_2$ represent 4-hydroxy; $R_3$ represents 3-hydroxy; $R_4$ represents 5-hydroxy; $R_5$ represents 6-hydroxy; and $R_6$ represents 2-carboxy.

$R_7$ preferably represents hydrogen.

$R_8$ preferably represents hydrogen.

A is preferably O.

The compounds of Formula I wherein A is oxygen are prepared from corresponding fused or bicyclic ring ketones by known processes such as shown in Scheme I, below. The starting fused or bicyclic ring ketones are known and described in published references or can be obtained readily. The benzophenone compound(s) is prepared as described in Examples 1 or 2.

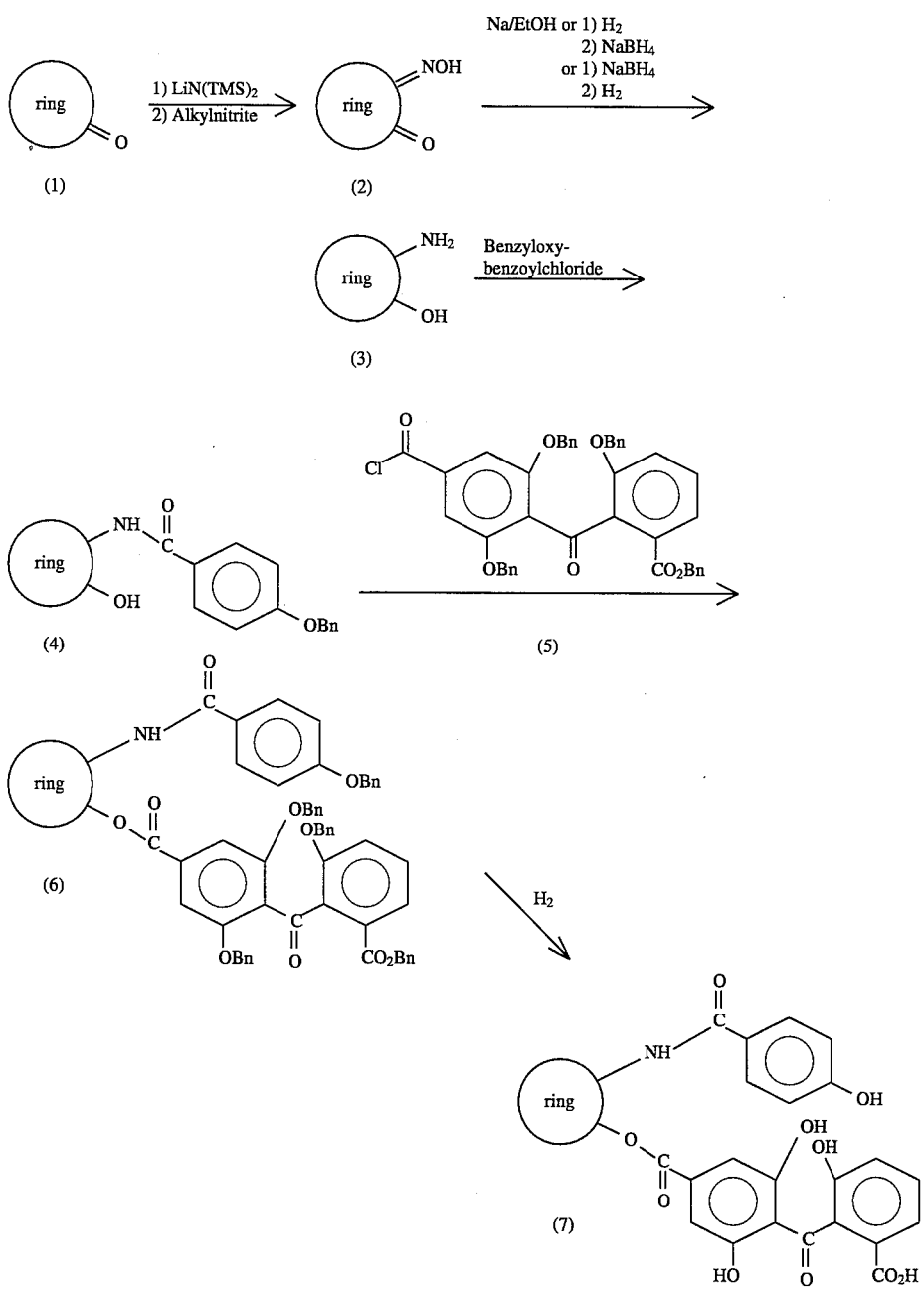

Scheme I

According to Scheme I, the starting fused or bicyclic ring ketones(1) are converted to the corresponding oximes (2) by treatment with, for example, lithium bis(trimethylsilyl)amide and an alkyl nitrite. The corresponding amino alcohols (3) are prepared either by reduction of oximes (2) with sodium in alcohol or in two steps by treatment with sodium borohydride and hydrogen/catalyst. Treatment of the amino alcohols (3) with benzyloxybenzoylchloride yields substituted benzylamide alcohols (4). Treatment of compounds (4) with substituted benzoylbenzoic acid chlorides (5) in methylene chloride yields formula (6) compounds which are reduced to produce formula (7) compounds which are compounds of Formula I.

Compounds of Formula I that are indane derivatives are prepared by treating starting indane epoxides with ammonia to yield amino indanols. The amino indanols then are converted to Formula I compounds using the process described in Scheme I. Compounds of Formula I having phenyl ring substituents other than those shown in compounds (7) are prepared by suitable modification of Scheme I or further processing of compounds (7). Formula I compounds where X is $CH_2$ are prepared as shown in Scheme I except that the substituted benzoylbenzoic acid chlorides are replaced by corresponding benzyl chlorides. An alternate synthesis is shown in Example 18.

Formula I compounds wherein A is $NR_8$ are prepared by modifying Scheme I as follows:

Scheme Ia

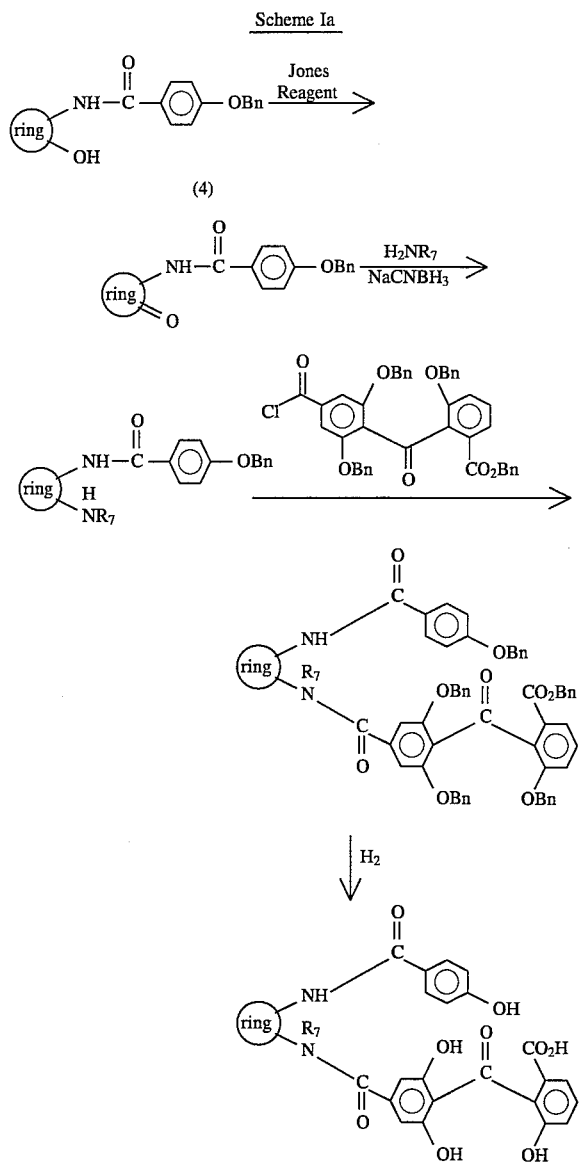

Pharmaceutically useful salts included in Formula I comprise, for example, sodium, potassium, trialkyl ammonium, calcium, zinc, lithium, magnesium, aluminium, diethanolamine, ethylenediamine, megulmine, acetate, maleate, fumarate, lactate, oxalate, methanesulfonate, ethanesulfonate, benzenesulfonate, tartrate, citrate, hydrochloride, hydrobromide, sulfate, phosphate, and nitrate.

The invention also includes compounds of the following Formula II which are useful in preparing the Formula I compounds:

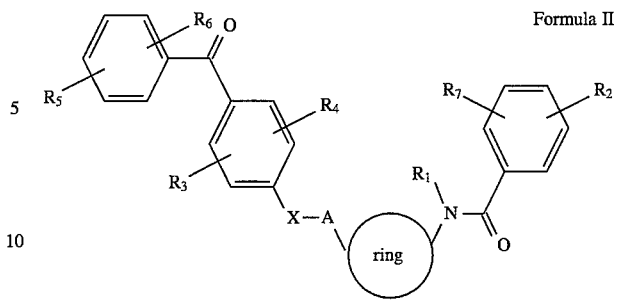

Formula II wherein:

is a fused or bridged bicyclic ring which includes (contains) 7–12 carbon atoms and may include (contains) one or more heteroatoms selected from the group of N, O and S;

X is

or $CH_2$;

A is O or $NR_8$; and $R_1$ and $R_8$ independently are H or lower alkyl;

$R_2$, $R_3$, $R_4$, $R_5$, $R_6$, and $R_7$ (when present) are any accessible combination of OBn, $CO_2Bn$, $OCH_2Oalkyl$, or $CO_2alkyl$.

As used herein, the term Bn means benzyl and the term alkyl in $OCH_2Oalkyl$ or $CO_2alkyl$ represents $C_{1-4}$ alkyl such as methyl or ethyl.

$R_7$ is preferably absent (represents hydrogen).

According to the invented methods Formula I compounds are used to treat diseases involving cellular growth, regulation, and differentiation such as inflammatory, cardiovascular, and neoplastic disease. As used herein inflammatory diseases include reperfusion injuries and psoriasis and other inflammatory skin diseases. Compounds of Formula I also are used to treat fungal and viral infections. Additionally, Formula I compounds are useful in treating various central nervous system disorders such as injuries induced by ischemia and Alzheimer's disease.

At least some of the compounds included in Formula I are PKC inhibitors and presently it is believed that PKC inhibition is important in producing the therapeutic effect produced by the Formula I compounds. Compounds that inhibit PKC are identified by an assay in which radiolabelled ATP is combined with a phosphorylation acceptor molecule in the presence of PKC and a compound being tested for potency in inhibiting PKC. Various levels of test compound are used to determine the level of inhibitory activity that a particular test compound possesses. As a control, radiolabelled ATP, phosphorylation acceptor molecule, and PKC are combined without test compound. Widely used methods for determining PKC inhibition have been described by A. C. McArdle and P. M. Conn, Methods in Enzymology (1989) 168, 287; and U. Kikkawa et al., Biochem. Biophys. Res. Commun. (1986) 135, 636 and are incorporated fully herein by reference.

The Formula I compounds that have been tested for PKC inhibitory activity have been found to have $IC_{50}$'s between 5 nM and 50 μM.

To investigate the effect that Formula I compounds have on cell growth and activity, assays are performed such as to determine growth inhibition of cultured tumor cells and cultured keritinocytes, and neutrophil superoxide anion release by well known techniques.

The $IC_{50}$'s found for selected compounds of the invention tested in these cells are shown in Table 1 below. Table 1 also includes data from testing in a cellular assay known as the "Bleb" assay. In the Bleb assay K562 cells, a human chronic myeloid leukemia cell line, are treated with compound and scored for the appearance of morphologic changes referred to as blebs on the cell surface. Previous studies have indicated that phorbol esters, PKC actuators, induce blebbing and staurosporine, a known PKC inhibitor, inhibits phorbol ester-induced blebbing. H. Osada et al., (1988) 41:7, 925.

TABLE 1

| | $IC_{50}$ of Compounds in Cells (μM) | | | |
|---|---|---|---|---|
| EXAMPLE | NEUTROPHILS | BLEB | NHEK | MCF-7 |
| 3 | | | 50 | 71 |
| 4 | | | 43 | 2.1–4.0 |
| 5 | | 50 | 5.0 | 23 |
| 8 | | 12.5 | 92 | 74 |
| 14 | 10 | | | |
| 16 | 10 | 25 | | |

Formula I compounds also have been tested in vivo to determine their antiinflammatory activity. The model used for this testing is the well-known, widely accepted phorbol ester-induced mouse ear edema model wherein the efficacy of a test compound to reduce the edema induced by the phorbol ester is measured. Using this testing paradigm the Formula I compounds of Examples 3, 5, 12, 13 and 16 were found to be active.

Formula I compounds are formulated into acceptable pharmaceutical compositions using well known pharmaceutical chemistry methods. For example, Formula I compounds are formulated into tablets, capsules, powders, elixirs, syrups, or emulsions for oral administration; sterile solutions or emulsions for parenteral administration; or ointments or creams for topical administration. In addition to the Formula I compounds the pharmaceutical compositions of the invention may include carriers such as water, oil, saline, lactose, sucrose, mannitol, starch, or magnesium stearate; coloring agents; flavoring agents; preservatives; and stabilizing agents. Certain of the pharmaceutical compositions are formulated to provide sustained release or are film coated.

Pharmaceutical compositions including Formula I compounds are administered orally, parenterally, topically, by inhalation, optically, otically, or rectally. It presently is contemplated that the daily dosage, which may be divided, will be in the range of from about 1 μg to about 1 mg per kg of body weight, preferably from about 1 μg to about 40 mg per kg of body weight, more preferably from about 10 μg to about 20 mg per kg of body weight. The optimum dosage for treatment of human diseases is readily determinable by standard clinical research techniques.

Prodrugs are compounds that upon administration are converted to Formula I compounds and thus are equivalents of the compounds disclosed and claimed herein. Prodrugs such as carbonates and carboxy esters of phenolic hydroxy and amino groups are prepared by derivatization of the hydroxy and amino groups with acylating agents, such as methyl chloroformate, ethyl chloroformate, isobutyroyl chloride, methoxypropionyl chloride, methyl chlorosuccinate, ethyl chlorosuccinate, and benzoyl chloride, for example.

The following examples illustrate preparation of Formula I compounds. These examples do not limit the scope of the present invention as described above and claimed below. As used herein, Hunig's base is N,N-disopropylethylamine; TPAP is tetrapropylammonium perruthenate; TBAF is tetrabutylammonium fluoride; TEMPO is 2,2,6,6-tetramethylpiperidine-N-oxide; pTSA $H_2O$ is p-toluenesulfonic acid monohydrate; DMAP is 4-dimethylaminopyridine; LAH is lithium aluminium hydride, MOMCL methoxymethylchloride; and $TMSCHN_2$ is trimethylsilyl-diazomethane; $TMSN_3$ is trimethylsilylazide;

EXAMPLE 1

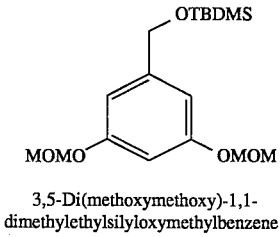

3,5-Di(methoxymethoxy)-1,1-dimethylethylsilyloxymethylbenzene

Benzophenone Reagent Preparation

MOMCl (29.8 mL, 0.393 mol) was added dropwise to a 0° C. solution of methyl 3,5-dihydroxybenzoate (30 g, 0.178 mol) and Hunig's base (57.6 g, 77.7 mL, 0.446 mol) in methylene chloride. After the final addition the reaction mixture was allowed to warm to ambient temperature and stirred overnight. This was poured into deionized water, the organics separated and washed with 10% aqueous copper sulphate solution. The organic layer was dried ($MgSO_4$), evaporated and chromatographed ($SiO_2$, 15:1 to 9:1 hexane-ethyl acetate, gradient elution). The major product was isolated as a clear colorless oil (34.5 g, 75%) and used as is in the next step.

The ester (36.0 g, 0.14 mol) was dissolved in anhydrous THF and added dropwise to a stirred solution of lithium aluminum hydride (183 mL of a 1.0M solution in THF) in dry THF. After the final addition stirring was continued for 2 h whereupon deionized water (8 mL), 15% aqueous NaOH (8 mL) and deionized water (28 mL) were sequentially added dropwise. The resulting suspension was stirred for 2 h and filtered. The solids were washed with ethyl acetate and the filtrates evaporated to provide the alcohol as a clear colorless oil (34 g) which was used in the next step without further purification.

A solution of TBDMSCl (23.3 g, 0.154 mol) in methylene chloride was added to a stirred mixture of imidazole (10.5 g, 0.154 mol) and the above prepared alcohol (32.06 g, 0.140 mol) in methylene chloride. The reaction mixture was allowed to stir at ambient temperature overnight and poured into deionized water. The organics were separated, washed with 10% aqueous copper sulphate solution, brine and dried (MgSO₄) and evaporated. The residue was chromatographed (SiO₂, 10:1 hexane-ethyl acetate) to provide the title compound as a clear colorless oil (38.9 g, 81%).

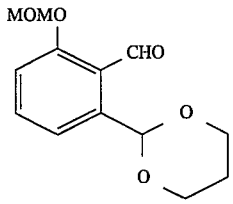

2-[2-Formyl-3-(methoxymethoxy)phenyl]-1,3-dioxane

N-BuLi (10.9 mL of a 1.6M solution in hexanes, 17.5 mmol) was added dropwise to a stirred solution of 2-[3(methoxymethoxy)phenyl]-1,3-dioxane (3.65 g, 15.9 mmol) in anhydrous cyclohexane at ambient temperature. The mixture (which gummed up) was stirred for 15 min whereupon dry DMF (3.69 mL, 47.6 mmol) was added dropwise and stirred for an additional 15 min, quenched upon addition of brine and diluted with ethyl acetate. The organics were separated and washed with brine and deionized water, dried (MgSO₄) and evaporated to a light yellow gum. The aldehyde (4.0 g, 100%) was used without further purification.

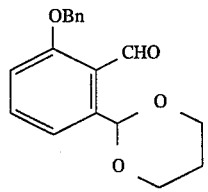

2-[2-Formyl-3-(benzyloxy)phenyl]-1,3-dioxane

N-BuLi (3.98 mL of a 1.6M solution in hexanes, 6.36 mmol) was added dropwise over 10–15 min to a solution of 2-[2-bromo- 3-(benzyloxy)phenyl]-1,3-dioxane (2.02 g, 5.78 mmol) in dry THF at −78° C. After the final addition the mixture was stirred for an additional 30 min whereupon anhydrous DMF (4.48 mL, 57.8 mmol; 10 equivalent) was added dropwise over a period of 10 min. The resulting solution was stirred at −78° C. for 4 hr and allowed to slowly warm to ambient temperature and allowed to stir overnight (16 h). The reaction was quenched upon addition of saturated ammonium chloride solution and diluted with ethyl acetate. The aqueous was separated and extracted with ethyl acetate. The combined organics were sequentially washed with brine and water several times, dried (MgSO₄) and evaporated to afford a gum which was chromatographed (SiO₂, 1:1 to 2:1 methylene chloride-hexanes, gradient elution) and the major component (title compound) isolated as an oil, which crystallised upon standing: mp 85°–7° C.

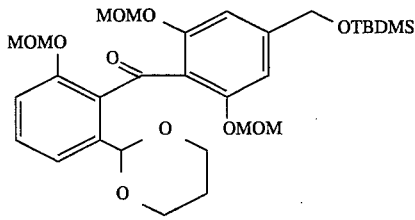

2'-(1,6-Dioxanyl)-6'-methoxymethoxy-2,6-di(methoxymethoxy)-4-(1,1-dimethylethylsilyloxymethyl)benzophenone N-BuLi (6.80 mL of a 1.6M solution in hexanes, 10.9 mmol) was added dropwise to a solution of 3,5-di(methoxymethoxy)-1,1-dimethylethylsilyloxy-methylbenzene (3.4 g, 9.93 mmol) in dry THF at 0° C. over a 5 min period. Stirring was then continued for 15 min whereupon this solution was added via cannula to a solution of the above prepared 2-[2-formyl-3-(methoxymethoxy)phenyl]-1, 3-dioxane (2.63 g, 10.4 mmol) in anhydrous THF at 0° C. The light yellow solution was then allowed to warm to ambient temperature and stirred overnight. This was quenched with brine and diluted with ethyl acetate. The layers were separated and the aqueous extracted with ethyl acetate. The combined organics were washed with brine, dried (MgSO₄) and evaporated. The residue was chromatographed (2:1 hexanes-ethyl acetate) to afford the major product alcohol as a gum (2.5 g, 41%). Some impure aldehyde (500 mg) was also recovered.

N-Methyl morpholine oxide (0.80 g, 6.81 mmol) was added to a mixture of the above prepared alcohol (2.7 g, 4.54 mmol) and crushed 4A molecular sieves (which had been placed in a 110° C. oven for several h) in dry methylene chloride. After 30 min TPAP (160 mg, 0.454 mmol) was added and the resulting solution stirred at ambient temperature for 2 days. Silica was added and the solvent removed in vacuo and placed on a dry packed column of silica and eluted with 3:1 hexane-ethyl acetate. The benzophenone (title compound) (2.34 g, 87%) was isolated as a clear colorless oil.

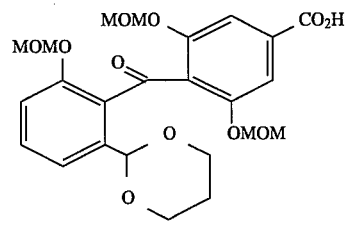

3,5-Di(methoxymethoxy)-4-[2-(methoxymethoxy)-6-(1,6-dioxanyl)benzoyl]benzoic acid Tetrabutylammonium fluoride (45.0 mL of a 1.0M solution in THF, 44.9 mmol) was added dropwise to a stirred solution of 2'-(1,6-dioxanyl)-6'-methoxymethoxy-2,6-di(methoxymethoxy)-4 -(1,1-dimethylethylsilyloxy-methyl-)benzophenone, prepared as above (22.2 g, 37.4 mmol) in anhydrous THF (150 mL). After stirring for 1 h the reaction was quenched with brine and diluted with ethyl acetate. The organics were separated and the aqueous layer extracted with ethyl acetate. The combined aqueous layers were also extracted with methylene chloride. The combined ethyl acetate extracts were backwashed with brine and added to the methylene chloride layer. These combined organics were dried (MgSO₄) and evaporated and the residue chromatographed (SiO, 2:1 ethyl acetate-hexanes) to provide the alcohol as an oil (13.0 g, 72%) which crystallised upon standing and was used in the next step without further purification.

Manganese dioxide (12 g) was added in portions to a stirred solution of the alcohol (14.1 g, 29.5 mmol) in methylene chloride. The mixture was stirred at ambient temperature for 2 days and the catalyst removed by filtration through Celite®. The catalyst was washed with further methylene chloride and the filtrates evaporated to afford the aldehyde as a white foam (12.2 g, 84%).

A solution of the above prepared aldehyde (12.2 g, 24.8 mmol) and NaH₂PO₄ (1.04 g, 8.67 mmol; 0.35 equiv.) in acetonitrile and deionized water (160 mL total volume; 6:1 v/v) was cooled in an ice-bath. Hydrogen peroxide (3 mL of a 30% solution on water) was added followed by solid sodium chlorite (4.4 g of 80%). This mixture was stirred for 1 h and the solvent was removed in vacuo. Deionized water was added and the precipitated solid collected by filtration. This was dried in vacuo to give the acid (9.11 g). The filtrates were extracted with methylene chloride, dried (MgSO$_4$), evaporated and crystallised from ethyl acetate-hexanes to provide acid (0.8 g). These solid materials were combined to give a total yield of 9.91 g (79%) of target acid (title compound): mp 152°–3° C.

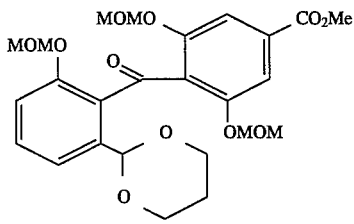

Methyl [3,5-Dimethoxymethoxy-4-(2-methoxy-methoxy)-6-(1,6-dioxanyl)benzoyl]benzoate TBAF (7.96 mL of a 1.0M solution in THF, 7.96 mmol) was added dropwise to a stirred solution of 2-(1,6-dioxanyl)-6'-methoxymethoxy- 2,6-di(methoxymethoxy)-4-)1,1-dimethylethylsilyloxymethyl)benzophenone, prepared as above (2.36 g, 3.98 mmol) in anhydrous THF at ambient temperature. After 1 h brine was added and diluted with ethyl acetate. The combined organics were separated and the aqueous layer extracted with more ethyl acetate. The combined organics were washed with brine, dried (MgSO$_4$) and evaporated to a gum (1.43 g, 75%). This material was used in the next step without further purification.

TEMPO (2.3 mg, 0.0148 mmol) was added to a solution of sodium bromide (46 mg, 0.445 mmol) and the above prepared alcohol (1.42 g, 2.97 mmol) in methylene chloride. The reaction mixture was placed in an ice bath and a freshly prepared solution of sodium bicarbonate (37 mg, 0.445 mmol) in Chlorox® (4 mL) was added dropwise. Stirring was continued for an additional 30 min whereupon the reaction was quenched with solid sodium sulfite. Deionized water was added to dissolve any suspended solids and the organic layer separated, dried (MgSO$_4$) and evaporated to afford the aldehyde (1.5 g) as a gum. This material was used in the next step without further purification.

A 0° C. solution of potassium hydroxide (0.41 g, 7.23 mmol) in methanol was added dropwise to a solution (0° C.) of the above prepared aldehyde (1.37 g, 2.78 mmol) in methanol. This was followed by the dropwise addition of a solution of iodine (0.92 g, 3.62 mmol) in methanol precooled to 0° C. After the final addition, the reaction mixture was warmed to ambient temperature and allowed to stir for 1 h, neutralised with 1N potassium hydrogen sulfate and the solvents were removed in vacuo. The residue was partitioned between ethyl acetate and brine. The organics were separated and washed with aqueous sodium thiosulfate, dried (MgSO$_4$) and evaporated. The residue was chromatographed (SiO$_2$, 8:5 hexane-ethyl acetate) and the ester (title compound) was isolated (819 mg) as a white foam. Alternatively this material could be concentrated and allowed to crystallise upon standing: mp 104°–5° C.

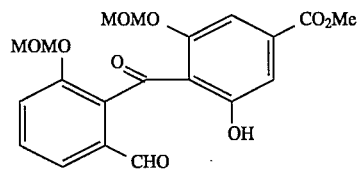

Methyl 4-[6-Formyl-2-methoxymethoxybenzoyl]-5-hydroxy-3-methoxymethoxybenzoate

A solution of the ester prepared in the previous step (1.65 g, 3.26 mmol) in methylene chloride was added to a stirred mixture of 18% sulphuric acid adsorbed on silica (ca. 12 g). The reaction mixture was stirred at ambient temperature for 10 h whereupon solid sodium carbonate was added, stirred for 5 min and filtered through a sintered funnel. The solid material was washed with methylene chloride and the filtrates were evaporated. The residue was crystallised from diethyl ether to afford aldehyde ester (title compound) (1.12 g, 63%) as a light yellow solid: mp 106°–8° C.

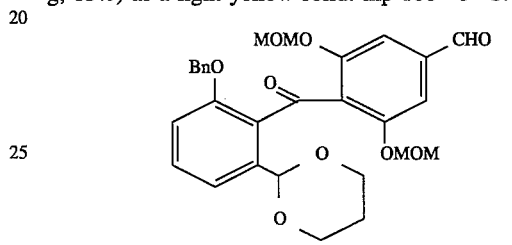

4-[(2-Benzyloxy)-6-(1,6-dioxanyl)benzoyl]-3,5-bismethoxymethoxy)benzaldehyde

N-BuLi (18.5 mL of a 2.5M solution in hexanes, 40.2 mmol) was added dropwise to a solution of MOM diether (15.8 g, 46.3 mmol) in dry THF at 0° C. over a 5 min period. Stirring was then continued for 60 min whereupon this solution was added via cannula to a solution of 2-[2-formyl-3-(benzyloxy)phenyl]-1,3-dioxane, prepared as above (12.0 g, 40.2 mmol) in anhydrous THF at 0° C. The light yellow solution was allowed to stir at 0° C. for 2 h and then allowed to warm to ambient temperature and stirring continued overnight. The reaction mixture was quenched with saturated ammonium chloride solution and diluted with ethyl acetate. The layers were separated and the aqueous layer extracted with ethyl acetate. The combined organics were washed with brine, dried (MgSO$_4$) and evaporated. The residue was chromatographed (2:1 hexanes-ethyl acetate) to afford the alcohol as a foam (18.8 g, 73%).

The alcohol above (18.7 g, 29.2 mmol) was dissolved in methylene chloride and MnO$_2$ (25.4 g, 0.292 mol) added in portions. The reaction mixture was allowed to stir overnight at ambient temperature at which time an additional 10 g of MnO$_2$ was added and stirring continued for 2 days. The catalyst was removed by filtration through Celite® and washed with more methylene chloride. The filtrates were evaporated to give the benzophenone (17.4 g, 93%) as a white foam.

TBAF (34.7 mL of a 1M solution in THF, 34.8 mmol) was added to a stirred solution of the above prepared benzophenone (18.5 g, 29.0 mmol) in anhydrous THF. After 1.5 h, brine was added and extracted twice with ethyl acetate. The aqueous layer was further extracted with methylene chloride and the ethyl acetate mixture backwashed with brine. The organics were all combined, dried (MgSO$_4$) and evaporated. The residue was chromatographed (SiO$_2$, 2:1 ethyl acetate-hexanes) to afford the alcohol (13.4 g, 88%) as a white solid: mp 130°–2° C.

MnO$_2$ (ca. 10 g) was added in portions to a stirred solution of the above alcohol (13.1 g) in methylene chloride and allowed to stir for 2 days at ambient temperature. The catalyst was removed by filtration through Celite® and the filtrates were evaporated to yield the aldehyde (title compound) (12.7 g, 97%) as a white solid: sample could be prepared by crystallisation from ethyl acetate: mp 134°–6° C.

EXAMPLE 2

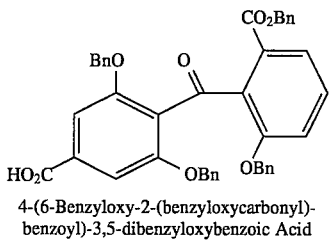

4-(6-Benzyloxy-2-(benzyloxycarbonyl)-
benzoyl)-3,5-dibenzyloxybenzoic Acid 2-(2-Bromo-3-benzyloxyphenyl)-1,3-dioxane (2-bromo-3-benzyloxy-benzyl alcohol (251 g, 0.86 mol) was dissolved in THF (300 mL) and sodium bromide (13.2 g, 0.128 mol) added. The reaction mixture was cooled to 0° C. and TEMPO (0.67 g, 4.28 mmol) was added followed by a freshly prepared (0° C.) solution of sodium bicarbonate (10.8 g, 0.128 mol) in 1 liter of commercial Chlorox® bleach. This was stirred rapidly at 0° C. for 3 h and sodium sulfite added. Any precipitated solids were dissolved upon addition of deionized water. The organics were separated and the aqueous layer extracted with ethyl acetate. The combined organics were washed with brine, dried (MgSO$_4$) and concentrated. The residue was cooled in an ice bath and the precipitated solids collected by filtration to give 2-bromo-3-benzyloxybenzaldehyde (224 g, 90%): mp 125°–6° C. The above prepared aldehyde (215 g) was combined in toluene (200 mL) with 1,3-propane diol (107 mL, 1.48 mol) and pTSA.H$_2$O (1.6 g) and heated at the reflux temperature with azeotropic removal of water via a Dean-Stark trap. After 1.5 h the reaction mixture was cooled and washed with saturated sodium bicarbonate and brine. The organics were separated, dried (MgSO$_4$) and evaporated. The residue was crystallized from methanol to afford the title compound as a white solid (248 g, 96%): mp 73°–4° C.

2-(2-Formyl-3-benzyloxyphenyl)-1,3-dioxane

N-BuLi (236.2 mL of a 1.6M solution in hexanes, 0.378 mmol) was added dropwise to a solution of the product of the preceding reaction (120 g, 0.344 mol) in dry THF (600 mL) at −78° C. The temperature was maintained <−60° C. during this time and stirring was continued for an additional 15 min after the final addition. Anhydrous DMF (532.2 mL, 6.87 mol) was then added dropwise while maintaining temperature <−60° C. The resulting solution was stirred at −60° C. for 4 h and allowed to slowly warm to ambient temperature and allowed to stir overnight (16 h). The reaction was quenched upon addition of saturation ammonium chloride solution and the solvents (THF, DMF) were removed in vacuo. The residue was partitioned between ethyl acetate and brine. The organics were sequentially washed with brine and water several times, dried (MgSO$_4$) and evaporated to a solid which was recrystallized from ethyl acetate-hexanes to give the title compound (80.7 g, 79%): mp 85°–7° C.

1,1,-Dimethylethyl 4-[2-benzyloxy-6-(1,6-dioxanyl)phenyl-hydroxy-methyl]-3,5-dibenzyloxybenzoate N-BuLi (77.86 mL of 2.5M solution in hexanes, 0.195 mol) was added dropwise to a −70° C. solution of 1,1-dimethylethyl 4-bromo-3,5-dibenzyloxybenzoate (83.1 g, 0.177 mol) in anhydrous THF (800 mL) at a rate to maintain the internal temperature <−65° C. After the final addition the mixture was stirred for a further 10 min, whereupon the purple colored solution was added quickly via cannula to a −70° C. solution of the aldehyde (44.0 g, 0.147 mol) in dry THF (800 mL). The resulting yellow reaction mixture was stirred at this temperature overnight at which time solid ammonium chloride was added and was then allowed to warm to ambient temperature. Deionized (700 mL) water was then added and the organic layer was separated. The aqueous was extracted with ethyl acetate and the combined organics were washed with brine, dried (MgSO$_4$) and evaporated to afford a yellow oil which was chromatographed (SiO$_2$, 15% ethyl acetate-hexanes). The title compound was isolated as a white foam (62.23 g, 61%).

1,1,-Dimethylethyl 4-[2-benzyloxy-6-(1,6-dioxanyl)benzoyl]-3,5-di-benzyloxybenzoate Manganese dioxide (250 g) was added in portions to a stirred solution of the product of the preceding reaction (62.2 g, 0.090 mol) in methylene chloride (1.5 L). The reaction mixture was allowed to stir overnight at ambient temperature and the MnO$_2$ was removed by filtration through Celite®. The pad was washed with further methylene chloride and the filtrates were evaporated to afford the title compound.

1,1,-Dimethylethyl 3,5-Dibenzyloxy-4-[6-benzyloxy-2-formyl-benzoyl]benzoate

The ketone product from the preceding reaction (58.0 g, 0.084 mol) was dissolved in acetone (270 mL) and deionized water (30 mL). A catalytic amount of pTSA.H$_2$O was added and the mixture refluxed for 3 h. Saturated sodium bicarbonate solution was added to adjust the pH to a basic level and the acetone was removed in vacuo. The aqueous layer was extracted with ethyl acetate and the organics dried (MgSO$_4$) and evaporated. The residue was crystallized from methanol to afford the title compound (50.48 g, 95%) as a light yellow solid.

3-Benzyloxy-2-[2,6-dibenzyloxy-4-(1,1-dimethylethoxy-carbonyl)-benzoyl]benzoic acid A solution of sulfamic acid (4.01 g, 0.041 mol) in deionized water (50 mL) was added to a solution of the aldehyde product of the previous reaction (20.0 g, 0.0318 mol) in acetonitrile (300 mL) at ambient temperature. After 5 min a solution of sodium chlorite (4.82 g, of 80%, 0.043 mol) in deionized water (50 mL) was added dropwise. Once complete the reaction mixture was stirred for 30 min. The solvent was removed in vacuo and the aqueous was extracted several times with ethyl acetate. The organics were combined, dried (MgSO$_4$) and evaporated to afford the title compound (20.9 g).

1,1-Dimethylethyl 4-(6-Benzyloxy-2-(benzyloxycarbonyl)-)benzoyl-3,5-dibenzyloxybenzoate To a solution of 5.98 g (9.28 mmol) of 3-benzyloxy-2-(2,6-dibenzyloxy-4-(1,1-dimethylethoxycarbonyl)benzoyl)benzoic acid in 75 mL of dry dimethylformamide was added 3.85 g (27.9 mmol) of potassium carbonate and 1.21 mL (1.74 g, 10.2 mmol) of benzyl bromide. The solution was stirred at room temperature under a nitrogen atmosphere for 13 h. The mixture was then poured onto 800 mL of water and extracted with three 400 mL portions of ether. The organic extracts were washed twice with water and then with brine, and dried over magnesium sulfate. Evaporation of the solvent afforded 6.76 g of the crude product, which was chromatographed on silica gel, eluting with 4/1 hexane-ethyl acetate to give 4.98 g (73%) of the title compound as a colorless oil.

4-(6-Benzyloxy-2-(benzyloxycarbonyl)benzoyl-3,5-dibenzyloxy-benzoic Acid

A solution of 0.428 g (0.582 mmol) of 1,1-dimethylethyl 4-(6-benzyloxy-2-(benzyloxycarbonyl)benzoyl-3,5-dibenzyloxybenzoate in 5 mL of distilled quinoline was heated at 200° C. under an atmosphere of nitrogen for 3 h. The mixture was then cooled, poured onto 75 mL of ether and washed three times with 2N HCl and once with brine. The organic extracts were dried over magnesium sulfate and evaporated to give 0.42 g of the crude product, which was recrystallized from isopropanol to give 0.270 g (68%) of the title compound as a tan solid, mp 151°–156° C.

EXAMPLE 3

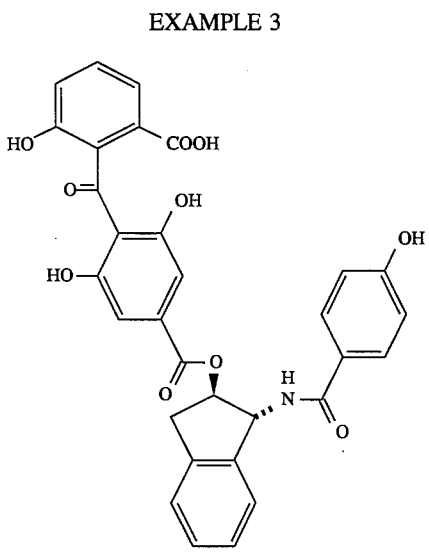

anti-1-(4-Hydroxybenzamido)-2-[3,5-dihydroxy-4-
(2-carboxy-6-hydroxy)benzoyl)benzoyloxy]indane anti-1-(4-Benzyloxybenzamido)-2-indanol 4-Benzyloxybenzoic acid (402 mg, 1.76 mmol) in CH$_2$Cl$_2$ (5 mL) was treated with catalytic DMF and oxalyl chloride (2.0M solution in CH$_2$Cl$_2$, 2.31 mL, 4.62 mmol) and stirred at room temperature for 1.5 h. Solvents were removed and the residue was taken into CH$_2$Cl$_2$ (10 mL) after drying over the vacuum for 1 h. To a biphasic mixture of 1-amino-2-indanol (250 mg, 1.68 mmol) in CH$_2$Cl$_2$ (30 mL) and 1.0N NaOH (9 mL) was added a solution of benzyloxybenzoyl chloride in CH$_2$Cl$_2$ (10 mL). The resulting mixture was vigorously stirred at room temperature for 3 h. The product was precipitated as white solids, which were collected and rinsed with CH$_3$OH (495 mg, 78%).

anti-1-(4-Hydroxybenzamido)-2-[3,5-dihydroxy-4-(2-carboxy-6-hydroxybenzoyl)benzoyloxy]indane To a solution of 4-(6-benzyloxy-2-(benzyloxycarbonyl)benzoyl)-3,5-dibenzyloxybenzoic acid (260 mg, 0.383 mmol) in CH$_2$Cl$_2$ (4 mL) was added cat. DMF and oxalyl chloride (2.0M solution in CH$_2$Cl$_2$, 479 mL, 0.958 mmol) at room temperature. The mixture was stirred at room temperature for 2 h. Solvents were removed and the acid chloride residue was taken into CH$_2$Cl$_2$ (5 mL) after drying over the vacuum for 1 h.

A solution of anti-1-(4-benzyloxybenzamido)-2-indanol (144.5 mg, 0.402 mmol), Et$_3$N (387.6 mg, 534 mL, 3.83 mmol) and DMAP (46.8 mg, 0.383 mmol) in CH$_2$Cl$_2$ (5 mL) was treated with the freshly made acid chloride-CH$_2$Cl$_2$ solution at 5° C. The reaction mixture was allowed to stir at room temperature for 3 h and then chromatographed on silica gel eluting with 3:2/hexane:EtOAc. The product was obtained as off-white solids.

The above intermediate (193 mg, 0.189 mmol) was dissolved in EtOAc-HOEt (2:1, 22.5 mL) and treated with 20% Pd(OH)$_2$/C (120 mg, 60 mol %). The mixture was subjected to hydrogenolysis at 50 psi for 20 h. Solvents were removed in vacuo and the residue taken into CH$_3$OH. The CH$_3$OH solution was concentrated after filtering through a pad of Celite® and chromatographed on a short silica gel column, eluting with 4:1/EtOAc:Hexane+0.5% HOAc. The title compound was obtained as yellow solids (79 mg, 73%); m.p. 176°–179 (dec)° C.

EXAMPLE 4

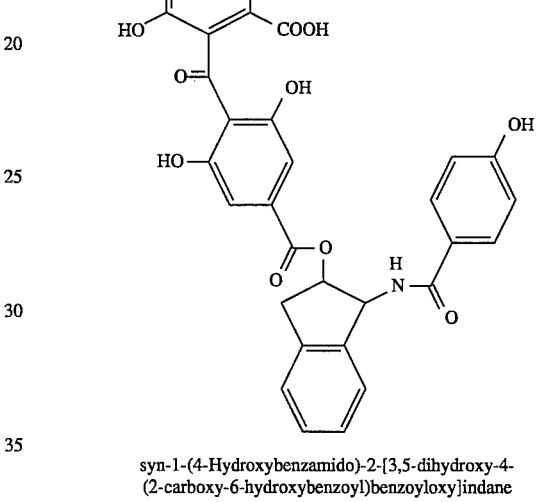

syn-1-(4-Hydroxybenzamido)-2-[3,5-dihydroxy-4-
(2-carboxy-6-hydroxybenzoyl)benzoyloxy]indane 1-(4-Benzyloxybenzamido)-2-indanone To a suspension of anti-1-(4-benzyloxybenzamido)-2-indanol (0.9 g, 2.5 mmol) in acetone (60 mL) was added Jones reagent portionwise (5 mL) at room temperature. The mixture was stirred at room temperature for 2 h. The color of Jones reagent no longer faded away and all the alcohol went into solution. Isopropanol (1 mL) was added to the mixture to consume excess Jones reagent. Solvents were removed in vacuo and the residue was taken into EtOAc and washed with water. The crude product was chromatographed on silica gel eluting with 3:1/Hexane:EtOAc to give white solids (410 mg, 46%).

syn-1-(4-Benzyloxybenzamido)-2-indanol

To a cold solution of 1-(4-benzyloxybenzamido)-2-indanone (530 mg, 1.48 mmol) in THF (50 mL) was added LiAl(OtBu)$_3$H (1.0M solution in THF, 2.3 mL, 2.39 mmol). The resulting yellow solution was stirred at room temperature for 2 h. 4 mL of 1N NaOH were added to the reaction mixture followed by 2 mL of H$_2$O. The slurry mixture was then diluted with EtOAc after stirring at room temperature for 30 min. The solids were filtered off and rinsed with EtOAc. The filtrate was washed with brine, dried over Na$_2$SO$_4$, and concentrated to dryness. Two sequential flash chromatographies (eluting with 5% to 10% acetone in CH$_2$Cl$_2$) gave a mixture of anti- and syn-isomers in a ratio of 1.75 to 1 (210:120 mg, 62%).

syn-(4-Hydroxybenzamido)-2-[3,5-dihydroxy-4-(2-carboxy-6-hydroxybenzoyl)benzoyloxy]indane To a solution of 4-(6-benzyloxy-2-(benzyloxycarbonyl)benzoyl)-3,5-dibenzyloxybenzoic acid (166 mg, 0,245 mmol) in CH$_2$Cl$_2$ (3 mL) was added cat. DMF and oxalyl chloride (2.0M solution in CH$_2$Cl$_2$, 306 µL, 0.612 mmol) at room temperature. The mixture was stirred at room temperature for 2 h. Solvents were removed and the acid chloride residue was taken into CH$_2$Cl$_2$ (5 mL) after drying over the vacuum for 1 h.

A solution of syn-1-(4-benzyloxybenzamido)-2-indanol (56 mg, 0.156 mmol), Et$_3$N (225 mg, 310 mL, 2.23 mmol) and DMAP (27.2 mg, 0.223 mmol) in CH$_2$Cl$_2$ (5 mL) was treated with the freshly made acid chloride-CH$_2$Cl$_2$ solution at 5° C. The reaction mixture was allowed to stir at room temperature for 3 h and then chromatographed on silica gel (eluting with 3:2/hexane:EtOAc). The product was obtained as yellow solids (135 mg, 85%).

The above intermediate (115 mg, 0.113 mmol) was dissolved in EtOAc-HOEt (2:1, 15 mL) and treated with 20% Pd(OH)$_2$/C (45 mg, 42 mol %). The mixture was subjected to hydrogenolysis at 50 psi for 18 h. Solvents were removed in vacuo and the residue taken up in CH$_3$OH. The CH$_3$OH solution was concentrated after filtering through a pad of Celite® and chromatographed on a short silica gel column (eluting with 4:1/EtOAc: Hexane+0.5% HOAc). The title compound was obtained as yellow solids (50 mg, 78%); m.p. 159°–161 (dec)° C.

EXAMPLE 5

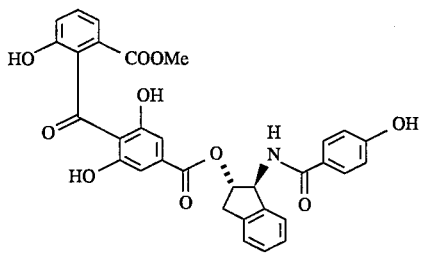

trans-1-(4-Hydroxybenzamido)-2-[3,5-dihydroxy-4-(2-hydroxy-6-methoxycarbonylbenzoyl)benzoyloxy]indane To a solution of 4-(6-benzyloxy-2-(benzyloxycarbonyl)benzoyl)-3,5-dibenzyloxybenzoic acid (2.1 g, 3.48 mmol) in CH$_2$Cl$_2$ (40 mL) was added cat. DMF and oxalyl chloride (2.0M solution in CH$_2$Cl$_2$, 4.34 mL, 8.68 mmol) at 5° C. The mixture was allowed to warm up to room temperature and stirred for 2 h. Solvents were removed and the acid chloride residue was taken into CH$_2$Cl$_2$ (60 mL) after drying over the vacuum for 1 h.

A slurry mixture of anti-1-(4-benzyloxybenzamido)-2-indanol (1.19 g, 3.31 mmol), Et$_3$N (3.35 g, 4.6 mL, 33.1 mmol) and DMAP (404.9 mg, 3.31 mmol) in CH$_2$Cl$_2$ (70 mL) was treated with the freshly made acid chloride-CH$_2$Cl$_2$ solution at 5° C. The reaction mixture was allowed to stir at room temperature overnight, followed by flash chromatography on silica gel (eluting with 3:2/hexane:EtOAc). The product was obtained as orange yellow solids (2.63 g, 84%).

The above intermediate (2.53 g, 2.65 mmol) was dissolved in MeOAc-CH$_3$OH (5:3, 80 mL) and treated with 20% Pd(OH)$_2$/C (1.1 g, 40 mol %). The mixture was subjected to hydrogenolysis at 50 psi for 17 h. Solvents were removed in vacuo and the residue taken into CH$_3$OH. The CH$_3$OH solution was concentrated after filtering through a pad of Celite® and chromatographed on a short silica gel column (eluting with 1:1/EtOAc: Hexane+0.5% CH$_3$OH). The title compound was obtained as yellow solids (1.3 g, 87%); m.p. 160°–162° C.

EXAMPLE 6

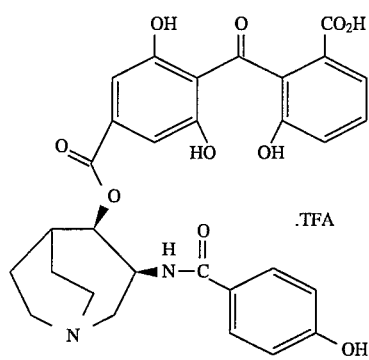

syn-4-[4-(2-Carboxy-6-hydroxybenzoyl)-3,5-dihydroxybenzoyloxy]-3-(4-hydroxybenzoylamino)-1-azabicyclo[3.2.2]nonane, trifluoroacetic acid salt 1-Azabicyclo[3.3.2]nonan-4-one An ice-cooled (5° C.) solution of tri-methylsilyldiazomethane/hexane (2N, 30 mL, 60 mmol) under nitrogen was treated dropwise with a solution of quinuclidin-3-one free base (from aqueous Na$_2$CO$_3$ neutralization of HCl salt followed by ether extraction, 6.26 g, 50 mmol) in anhydrous tetrahydrofuran (40 mL). Methanol (20 mL) was added, and the yellow solution was warmed to room temperature, stirred for 16 h, and quenched to colorless by addition of acetic acid (~20 drops). After a few min saturated sodium carbonate (15 mL) was added. The organic (top) layer was separated and the aqueous solution was extracted with methylene chloride (3×50 mL). The combined organic layer and extracts were dried (Mg$_2$SO$_4$), concentrated in vacuo, dissolved in minimal methylene chloride, and filtered through a short column of alumina (eluted with 2% methanol/methylene chloride). The filtrate was concentrated in vacuo to afford 1-azabicyclo[3.2.2]nonan-4-one (5.12 g, 74%) as an amorphous white solid.

1-Azabicyclo[3.3.2]nonan-3,4-dione-3-oxime

A solution of 1-azabicyclo[3.2.2]nonan-4-one (1.39 g, 10 mmol) in anhydrous tetrahydrofuran (20 mL) under nitrogen was cooled (−65° C.), and treated with n-butyl nitrite (1.30 mL, 11 mmol). 1.0N Lithium bis(trimethylsilyl)amide/THF (16 mL, 16 mmol) was added dropwise so as to keep the pot temperature below −58° C. After the addition was complete the mixture was warmed to room temperature over one h, stirred for 30 min, cooled on an ice bath, and treated with saturated ammonium chloride (6 mL). The solution was concentrated in vacuo, diluted with toluene, and reconcentrated to remove most of the water. The residue was chromatographed on silica gel (eluted with 5% methanol/methylene chloride, then with 10% methanol/methylene chloride), then triturated from ether to afford 1-azabicyclo[3.2.2]nonan-3,4-dione-3-oxime (0.92 g, 55%) as a white solid.

4-Hydroxy-3-(4-phenylmethoxybenzoylamino)-1-azabicyclo[3.2.2]-nonane, mixture of isomers An ice-cooled (5° C.) suspension of 1-azabicyclo-[3.2.2]nonan-3,4-dione-3-oxime (0.336 g, 2.0 mmol) in methanol (4 mL) was treated with sodium borohydride (0.11 g, 2.9 mmol), then stirred at room temperature for one h. Water (0.25 mL) was added, and the mixture was concentrated in vacuo, diluted with toluene, and reconcentrated. The residue was dissolved in methanol (20 mL), placed in a Parr bottle, treated with Raney Nickel (one-half tsp.), and hydrogenated at 45–50 psi for 16 h. The mixture was evacuated of hydrogen and filtered through Celite® (filter cake washed with methanol, but not to dryness). The filtrate was concentrated in vacuo, diluted with toluene, and reconcentrated (put aside under nitrogen). Meanwhile, a solution of 4-benzyloxybenzoic acid (0.69 g, 3.0 mmol) in anhydrous methylene chloride (8 mL) was treated with N,N-dimethylformamide (0.2 mL), then with 2.0N oxalyl chloride/methylene chloride (2.0 mL, 4.0 mmol), and the mixture was stirred under nitrogen for one h. The solution was concentrated in vacuo, diluted with anhydrous toluene (20 mL), reconcentrated, and placed under high vacuum for one h. The residue was dissolved in anhydrous toluene (10 mL) and combined with the aminoalcohol set aside above, then treated with 1.0N sodium hydroxide (5 mL) and vigorously stirred for 3.5 h at room temperature.

A few mL of 2-propanol was added, and the organic layer was separated. The aqueous layer was extracted with toluene (15 mL) containing a few mL of 2-propanol, and the combined organic layer and extract were concentrated in vacuo and dissolved in methanol (8 mL). Aqueous potassium hydroxide (30%, 3.0 mL) was added, and the mixture was stirred for 1.5 h and concentrated in vacuo, then diluted with water (10 mL) and extracted with toluene (2×15 mL) containing some 2-propanol. The combined organic extracts were dried (Na$_2$SO$_4$) and concentrated in vacuo to a white solid, which was triturated from ether to afford 4-hydroxy-3-(4-phenylmethoxybenzoylamino)-1-azabicyclo[3.2.2] nonane, mixture of isomers (0.379 g, 52%, predominantly syn isomer).

syn-4-[4-(2-Benzyloxycarbonyl-6-phenylmethoxybenzoyl)-3,5-bis-(phenylmethoxy) benzoyloxy]-3-(4-phenylmethoxybenzoylamino)-1-azabicyclo[3.2.2]nonane A solution of 4-(6-benzyloxy-2-(benzyloxy-carbonyl)benzoyl-3,5-dibenzyloxybenzoic acid (0.373 g, 0.55 mmol) in anhydrous methylene chloride (2.0 mL) was treated with N,N-dimethylformamide (4 drops), then with 2.0N oxalyl chloride/methylene chloride (0.40 mL, 0.80 mmol), and stirred under nitrogen for one h. The solution was concentrated in vacuo, placed under high vacuum for one h and set aside.

A solution of 4-hydroxy-3-(4-phenylmethoxybenzoylamino)-1-aza-bicyclo[3.2.2]nonane, mixture of isomers (0.183 g, 0.50 mmol) in 2:1 tetrahydrofuran/N,N-dimethylformamide (1.5 mL) was treated with 4-dimethylaminopyridine (40 mg) and triethylamine (1.0 mL). The acid chloride prepared above was dissolved in 2:1 tetrahydrofuran/N,N-dimethylformamide (1.5 mL) and combined with this solution, and the mixture was stirred under nitrogen for 24 h and diluted with toluene (25 mL). The organic solution was washed with 0.5N sodium hydroxide (15 mL), then with water (15 mL), dried (Na$_2$SO$_4$), and concentrated in vacuo. Silica gel chromatography (eluted initially with 85:15 EtOAc/IPA, then with 80:15:5 EtOAc/IPA/triethylamine) afforded first syn-4-[4-(2-benzyloxycarbonyl-6-phenylmethoxybenzoyl)-3,5-bis(phenylmethoxy)benzoyloxy]-3-(4-phenylmethoxybenzoylamino)-1-azabicyclo[3.2.2] nonane (160 mg), then anti-4-[4-(2-benzyloxycarbonyl-6-phenylmethoxybenzoyl)-3,5-bis(phenylmethoxy)-benzoyloxy]-3-(4-phenylmethoxybenzoylamino)-1-azabicyclo[3.2.2]nonane (47 mg); total yield of both isomers was 207 mg (40%).

syn-4-[4-(2-Carboxy-6-hydroxybenzoyl)-3,5-dihydroxybenzoyloxy]-3-(4-hydroxybenzoylamino)-1-azabicyclo [3.2.2]nonane, trifluoroacetic acid salt A solution of syn-4-[4-(2-benzyloxycarbonyl-6-phenylmethoxybenzoyl)-3,5-bis(phenylmethoxy)benzoyloxy]-3-(4-phenylmethoxybenzoylamino)-1-azabicyclo[3.2.2] nonane (150 mg, 0.146 mmol) in reagent ethanol (6 mL) in a 25 mL 2-neck flask was treated with trifluoroacetic acid (30 mL, 0.38 mmol), then with 20% Pd(OH)$_2$/C (80 mg). The flask was quickly fitted with a balloon valve with a balloon, and purged with hydrogen, then stirred under hydrogen for 48 h.

The flask was evacuated of hydrogen, the solution was filtered through Celite®, and the filter cake was washed with ethanol (do not let dry). The filtrate was concentrated in vacuo, and the residue found (by NMR analysis) to contain benzylated intermediates. Thus, it was dissolved in ethanol (20 mL) in a Parr bottle, treated with 20% Pd(OH)$_2$/C (80 mg), and subjected to hydrogenation at 50 psi in a Parr apparatus for 14 h. The bottle was evacuated of hydrogen, the solution filtered through Celite®, and the filter cake washed with ethanol (do not allow to dry). The filtrate was concentrated in vacuo and the residue was dissolved in DMF (0.4 mL) and loaded onto an HPLC column; conditions: A-0.1% TFA/5% MeCN/H20, B-MeCN, 100% A to 50:50 A:B over 60 min, 15 mL/min, 21×250 cm C$_{18}$ column. Fractions (one/min) 27–32 were combined, partially concentrated, and freeze-dried overnight to afford syn-4-[4-(2-carboxy-6-hydroxybenzoyl)-3,5-dihydroxybenzoyloxy]-3-(4-hydroxy-benzoylamino)-1 -azabicyclo[3.2.2]nonane, trifluoroacetic acid salt (48 mg, 41%) as a voluminous yellow solid; m.p. 270°–275° C. (dec).

EXAMPLE 7

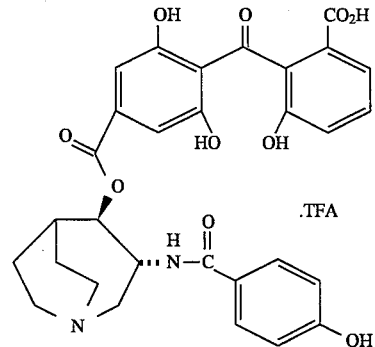

anti-4-[4-(2-Carboxy-6-hydroxybenzoyl)-3,5-dihydroxybenzoyloxy]-3-(4-hydroxybenzoylamino)-1-azabicyclo[3.2.2]nonane, trifluoroacetic acid salt anti-4-[4-(2-Carboxy-6-hydroxybenzoyl)-3,5-dihydroxybenzoyloxy]-3-(4-hydroxybenzoylamino)-1-azabicyclo [3.2.2]nonane, trifluoroacetic acid salt A solution of anti-4-[4-(2-benzyloxycarbonyl-6-phenylmethoxybenzoyl)-3,5-bis(phenylmethoxy)benzoyloxy]-3-(4-phenylmethoxybenzoylamino)-1-azabicyclo[3.2.2] nonane (45 mg, 0.044 mmol) in reagent ethanol (5 mL) in a 25 mL 2-neck flask was treated with trifluoroacetic acid (40 mL), then with 20% Pd(OH)$_2$/C (80 mg). The flask was quickly fitted with a balloon valve with a balloon, and purged with hydrogen, then stirred under hydrogen for 20 h. The flask was carefully evacuated of hydrogen, the solution was filtered through Celite®, and the filter cake was washed with ethanol (do not let dry). The filtrate was concentrated in vacuo and the residue was dissolved in DMF (0.4 mL) and loaded onto an HPLC column; conditions: A-0.1%TFA/5% MeCN/H$_2$O, B-MeCN, 100% A to 50:50 A:B over 60 min, 15 mL/min, 21×250 cm C$_{18}$ column. Fractions (one/min) 29–31 were combined, partially concentrated, and freeze-dried overnight to afford anti-4-[4-(2-carboxy-6-hydroxybenzoyl)-3,5-dihydroxybenzoyloxy]-3-(4-hydroxybenzoylamino)-1-azabicyclo[3.2.2]nonane, trifluoroacetic acid salt (7.6 mg, 22%) as a voluminous yellow solid; m.p. 260°–265° C. (dec).

EXAMPLE 8

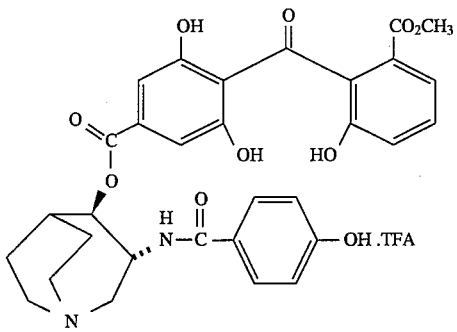

anti-4-[4-(2-Methoxycarbonyl-6-hydroxybenzoyl)-
3,5-dihydroxybenzoyloxy]-3-(4-hydroxybenzamido)-
1-azabicyclo[3.2.2]nonane, trifluoroacetic acid salt An ice-cooled (5° C.) solution of anti-4-[4-(2-carboxy-6-hydroxybenzoyl)-3,5-dihydroxybenzoyloxy]-3-(4-hydroxybenzamido)-1-azabicyclo[3.2.2]-nonane, trifluoroacetic acid salt (Example 5, 11.0 mg, 0.0145 mmol) in anhydrous methanol (0.2 mL) under nitrogen was treated via microsyringe with thionyl chloride (10 mL, 0.137 mmol, 9.5 eq). The mixture was warmed to 50° C. over 20 min and stirred at 50° C. for 3 h. The reaction was incomplete by TLC, so the solution was recooled on an ice bath and treated with additional thionyl chloride (10 mL), then warmed to 50° C. for 2 h. The solution was concentrated in vacuo and the residue was dissolved in N,N-dimethylformamide (0.3 mL) and loaded onto HPLC; conditions: A- 0.1% TFA/5% $CH_3CN/H_2O$, B- $CH_3CN$, 100% A to 50% A:50% B over one h, 15 mL/min, 21×250 cm $C_{18}$ column. Fractions (one/min) 36–38 were combined, partially concentrated in vacuo, and freeze-dried over 3 h to afford anti-4-[4-(2-methoxycarbonyl-6-hydroxybenzoyl)-3,5-dihydroxybenzoyloxy]-3-(4-hydroxybenzamido)-1-azabicyclo[3.2.2]nonane, trifluoroacetic acid salt (5.2 mg, 46%) as a voluminous yellow solid; m.p. 250° C. (dec).

EXAMPLE 9

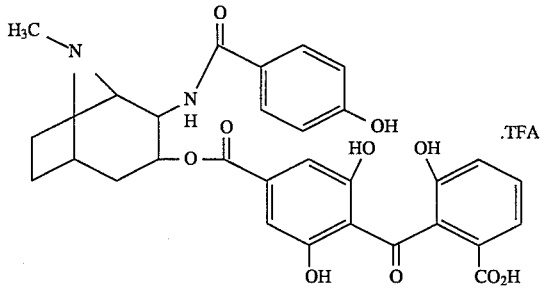

syn-3-[4-(2-Carboxy-6-hydroxybenzoyl)-3,5-dihydroxy-
benzoyloxy]-2-(4-hydroxybenzamido)-8-methyl-
8-azabicyclo[3.2.1]octane, trifluoroacetic acid salt 8-Methyl-8-azabicyclo[3.2.1]octan-2,3-dione-2-oxime A solution of 8-methyl-8-azabicyclo[3.2.1]octan-3-one (2.79 g, 20 mmol) in anhydrous tetrahydrofuran (40 mL) under nitrogen was cooled (−68° C.) and treated (via syringe) with 1.0N lithium bis(trimethylsilyl)amide/tetrahydrofuran (36 mL, 36 mmol) at a rate to keep the pot temperature below −55° C. The mixture was warmed to 0° C., then recooled (−68° C.), and treated dropwise with a solution of n-butyl nitrite (2.6 mL, 22 mmol) in anhydrous tetrahydrofuran (15 mL) at a rate to keep the pot temperature below −60° C. The mixture was warmed to room temperature over one h, stirred for one h, and quenched with saturated ammonium chloride (15 mL). The organic layer was separated and the aqueous solution was extracted with toluene (50 mL) containing some 2-propanol. The combined organic solution was dried ($Na_2SO_4$) and concentrated in vacuo. The residue was chromatographed on silica gel (eluted with 9:1 ethyl acetate/methanol, then with 3:2 ethyl acetate/methanol) to afford, first, 8-methyl-8-azabicyclo[3.2.1]octane-2,3-dione-2-oxime (0.43 g, 13%, beige solid), then recovered starting material (1.40 g). Product yield was 26% based on recovered starting material.

2-Acetamido-8-methyl-8-azabicyclo[3.2.1]octan-3-one

A solution of 8-methyl-8-azabicyclo[3.2.1]octane-2,3-dione-2-oxime (0.93 g, 5.5 mmol) in acetic acid/acetic anhydride (4:1, 40 mL) in a Parr bottle was treated with Raney nickel (Aldrich, ½ tsp.), then subjected to hydrogenation in a Parr apparatus at 45–50 psi for 5 h The solution was carefully evacuated of hydrogen, filtered through Celite® (wash filter cake carefully with methanol), and the filtrate was concentrated in vacuo. The residue was taken up in toluene and reconcentrated to remove most of the acetic acid. This residue was taken up in saturated sodium carbonate (40 mL), then treated with 15% sodium hydroxide (2 mL) and extracted with methylene chloride (3×50 mL) containing some 2-propanol. The combined extracts were dried ($Na_2SO_4$), concentrated in vacuo, and chromatographed on silica gel (eluted with 1:1 ethyl acetate/methanol) to afford a white solid, which contained some silica gel. This was removed by dissolving the product in warm ethyl acetate, filtering, and concentration in vacuo to afford 2-acetamido-8-methyl-8-azabicyclo[3.2.1]octan-3-one (0.53 g, 49%) as a white solid.

2-(4-Benzyloxybenzamido)-8-methyl-8-azabicyclo[3.2.1]octan-3-ol

An ice-cooled (5° C.) solution of 2-acetamido-8-methyl-8-azabicyclo[3.2.1]octan-3-one (0.393 g, 2.0 mmol) in anhydrous tetrahydrofuran (4 mL) under nitrogen was treated dropwise (via syringe) with 1.0N lithium tri (t-butoxy) aluminum hydride/tetrahydrofuran (Aldrich, 3.5 mL, 3.5 mmol), and the solution was stirred on the ice bath for 30 min and at room temperature for 45 min. The mixture was cooled (5° C.), then water (0.15 mL), 15% aqueous sodium hydroxide (0.15 mL), and water (0.45 mL) were added dropwise. The suspension was filtered and the solids were rinsed with tetrahydrofuran/2-propanol. The filtrate was concentrated in vacuo to a residue, which still contained aluminum salts, but was taken up in 2:1:1 water/ethanol/concentrated HCl (10 mL) and refluxed for three h. The mixture was exhaustively concentrated in vacuo to afford crude aminoalcohol dihydrochloride, which was taken up in toluene (10 mL) and treated with 2.5N sodium hydroxide (5 mL) and 4-benzyloxybenzoyl chloride (0.74 g, 3.0 mmol). The mixture was stirred for 18 h, then water (15 mL), toluene (25 mL), and 2-propanol (15 mL) were added, and the layers were partitioned. The aqueous layer was extracted with toluene (2×25 mL) containing some 2-propanol, and the combined organic solution was concentrated in vacuo and dissolved in methanol (8 mL). Water (2 mL) and potassium hydroxide (1.0 g) were added, and the mixture was stirred for 3 h and partially concentrated in vacuo to remove most of the methanol, then diluted with water (15 mL). The aqueous solution was extracted with toluene (3×40 mL) containing some 2-propanol, and the combined organic solution was dried ($Na_2SO_4$) and concentrated in vacuo. The residue was chromatographed on silica gel (eluted with 6:3:1 ethyl acetate/2-propanol/triethylamine, mixed fractions rechromatographed) to afford anti-2-(4-benzyloxybenzamido)-8-methyl-8-azabicyclo[3.2.1]octan-3-ol (0.44 g) as a white solid, then syn-2-(4-benzyloxybenzamido)-8-methyl-8-azabicyclo[3.2.1]octan-3-ol (0.22 g) as a pale yellow oil, which could be crystallized from ethanol. The total product yield was 0.66 g (90%).

syn-3-[4-(2-benzyloxycarbonyl-6-phenylmethoxybenzoyl)-3,5-bis(phenylmethoxy)benzoyloxy]-2-(4-phenylmethoxy-benzamido)-8-methyl-8-azabicyclo[3.2.1]octane A solution of 4-(6-benzyloxy-2-(benzyloxy-carbonyl)benzoyl)-3,5-dibenzyloxybenzoic acid (0.27 g, 0.40 mmol) in anhydrous methylene chloride (2.0 mL) was treated with N,N-dimethyl-formamide (3 drops), then with 2.0N oxalyl chloride/methylene chloride (0.35 mL, 0.70 mmol), and stirred for one h under nitrogen. The solution was concentrated in vacuo, placed under high vacuum for one h, then taken up in tetrahydrofuran (0.5 mL) and N,N-dimethylformamide (0.5 mL) under nitrogen. Triethylamine (0.5 mL) and 4-dimethylaminopyridine (30 mg) were added, followed closely by syn-2-(4-benzyloxybenzamido)-8-methyl-8-azabicyclo[3.2.1]octan-3-ol (0.090 g, 0.245 mmol). The solution was stirred at room temperature for 18 h, then diluted with toluene (20 mL). The organic solution was washed with 0.5N sodium hydroxide (10 mL), then with water (10 mL), dried ($Na_2SO_4$), and concentrated in vacuo. Silica gel chromatography (eluted with 93:5:2 ethyl acetate/2-propanol/triethylamine) afforded syn-3-[4-(2-benzyloxycarbonyl-6-phenylmethoxybenzoyl)-3,5-bis(phenylmethoxy)benzoyloxy]-2-(4-phenylmethoxybenzamido)-8-methyl-8-azabicyclo[3.2.1]octane (0.19 g, 75%) as a viscous glass.

syn-3-[4-(2-Carboxy-6-hydroxybenzoyl)-3,5-dihydroxybenzoyloxy]-2-(4-hydroxybenzamido)-8-methyl-8-azabicyclo[3.2.1]octane, trifluoroacetic acid salt A solution of syn-3-[4-(2-benzyloxycarbonyl-6-phenylmethoxybenzoyl)-3,5-bis(phenylmethoxy)benzoyloxy]-2-(4-phenylmethoxy-benzamido)-8-methyl-8-azabicyclo[3.2.1]octane (0.18 g, 0.175 mmol) in ethanol (22 mL) in a Parr bottle was treated with trifluoroacetic acid (0.11 mL) and purged with nitrogen. Pearlman's catalyst (130 mg) was added, and the bottle was promptly charged with hydrogen (44 psi) and shaken on a Parr apparatus for 18 h. The bottle was carefully evacuated of hydrogen, the solution was filtered through Celite®, and the filter cake was washed with ethanol (not allowed to dry). The filtrate was concentrated in vacuo and redissolved in N,N-dimethylformamide (0.75 mL), then loaded onto HPLC; conditions: A- 0.1% TFA/5% $CH_3CN/H_2O$, B- $CH_3CN$, 100% A to 50:50 A:B over one h, 25 mL/min, 41×250 mm $C_{18}$ column. Fractions (one/min) 36–41 were combined, partially concentrated in vacuo, and freeze dried overnight to afford syn-3-[4-(2-carboxy-6-hydroxybenzoyl)-3,5 -dihydroxybenzoyloxy]-2-(4-hydroxybenzamido)-8-methyl-8-azabicyclo[3.2.1]octane, trifluoroacetic acid salt (0.111 g, 85%) as a voluminous pale yellow solid; m.p. 200°–250° C. (dec).

EXAMPLE 10

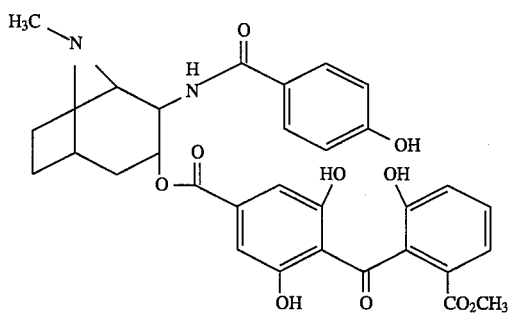

anti-2-(4-Hydroxybenzamido)-3-[4-(2-methoxycarbonyl-6-hydroxybenzoyl)-3,5-dihydroxybenzoyloxy]-8-methyl-8-azabicyclo[3.2.1]octane A solution/suspension of anti-3-[4-(2-carboxy-6-hydroxybenzoyl)-3,5-dihydroxybenzoyloxy]-2-(4-hydroxybenzamido)-8-methyl-8-azabicyclo[3.2.1]-octane, trifluoroacetic acid salt (33 mg, 0.050 mmol) in anhydrous methanol (0.60 mL) was cooled to −15° C. under nitrogen and treated dropwise (via microsyringe) with thionyl chloride (0.060 mL, 0.82 mmol). The temperature was warmed to 50° C. over 30 min and stirred at 50° C. for 4 h, then concentrated in vacuo. The residue was dissolved in N,N-dimethylformamide (0.30 mL) and loaded onto HPLC; conditions: A- 0.1% TFA/5% $CH_3CN/H_2O$, B- $CH_3CN$, 100% A to 50:50 A:B over one h, 15 mL/min, 21×250 mm $C_{18}$ column. Fractions (one/min) 29–33 were combined, partially concentrated, and freeze-dried over 18 h to afford anti-2-(4-hydroxybenzamido)-3-[4-(2-methoxycarbonyl-6-hydroxybenzoyl)-3,5-dihydroxybenzoyloxy]-8-methyl-8-azabicyclo[3.2.1]octane (27.5 mg, 93%) as a voluminous pale yellow solid; m.p. 180°–190° C. (dec).

EXAMPLE 11

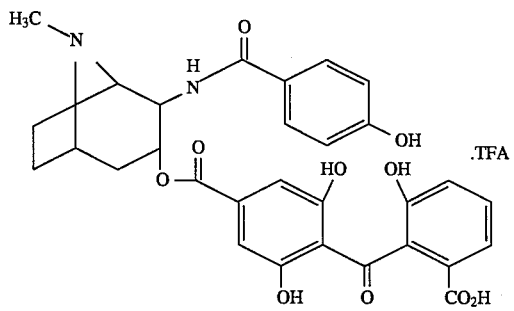

anti-3-[4-(2-Carboxy-6-hydroxybenzoyl)-3,5-dihydroxybenzoyloxy]-2-(4-hydroxybenzamido)-8-methyl-8-azabicyclo[3.2.1]octane, trifluoroacetic acid salt anti-3-[4-(2-Benzyloxycarbonyl-6-phenylmethoxybenzoyl)-3,5-bis-(phenylmethoxy)benzoyloxy]-2-(4-phenylmethoxybenzamido)-8-methyl-8-azabicyclo[3.2.1]octane A solution of 4-(6-benzyloxy-2-(benzyloxy-carbonyl)benzoyl)-3,5-dibenzyloxybenzoic acid (0.34 g, 0.50 mmol) in anhydrous methylene chloride (2.0 mL) was treated with N,N-dimethylformamide (4 drops), then with 2.0N oxalyl chloride/methylene chloride (0.40 mL, 0.80 mmol), and stirred for one h under nitrogen. The solution was concentrated in vacuo, placed under high vacuum for one h, then taken up in tetrahydrofuran (1.2 mL) and N,N-dimethylformamide (0.75 mL) under nitrogen. Triethylamine (0.75 mL) and 4-dimethylaminopyridine (50 mg) were added, followed closely by anti-2-(4-benzyloxybenzamido)-8-methyl-8- azabicyclo[3.2.1]octan-3-ol (0.147 g, 0.40 mmol). The solution was stirred at room temperature for 90 h, and much starting material remained unreacted; nevertheless, the solution was diluted with toluene (25 mL) containing some 2-propanol, washed with 0.5N sodium hydroxide (15 mL), then with water (15 mL), dried (Na$_2$SO$_4$), and concentrated in vacuo. Silica gel chromatography (eluted first with 85:10:5 ethyl acetate/2-propanol/triethylamine, then with 60:30:10 ethyl acetate/2-propanol/triethylamine) afforded anti-3-[4-(2-benzyloxycarbonyl-6-phenylmethoxybenzoyl)-3,5bis(phenylmethoxy)benzoyloxy]-2-(4-phenyl-methoxybenzamido)-8-methyl-8-azabicyclo[3.2.1]octane (0.13 g, 32%, glassy foam) followed by recovered starting alcohol (0.088 g). The yield based on recovered starting material was 79%.

anti-3-[4-(2-Carboxy-6-hydroxybenzoyl)-3,5-dihydroxy-benzoyloxy]-2-(4-hydroxybenzamido)-8-methyl-8-azabicyclo[3.2.1]octane, trifluoroacetic acid salt A solution of anti-3-[4-(2-benzyloxycarbonyl-6-phenyl-methoxybenzoyl)-3,5-bis(phenylmethoxy)benzoyloxy]-2-(4-phenyl-methoxybenzamido)-8-methyl-8-azabicyclo[3.2.1]octane (0.23 g, 0.224 mmol) in ethanol (25 mL) in a Parr bottle was treated with trifluoroacetic acid (0.12 mL) and purged with nitrogen. Pearlman's catalyst (140 mg) was added, and the bottle was promptly charged with hydrogen and shaken on a Parr apparatus for 18 h. The bottle was carefully evacuated of hydrogen, the solution was filtered through Celite®, and the filter cake was washed with ethanol (not allowed to dry). The filtrate was concentrated in vacuo and re-dissolved in N,N-dimethylformamide (0.75 mL), then loaded onto HPLC; conditions: A- 0.1% TFA/5% CH$_3$CN/H$_2$O, B- CH$_3$CN, 100% A to 100% B over one h, 15 mL/min, 41×250 mm C$_{18}$ column. Fractions (one/min) 36–39 were combined, partially concentrated in vacuo, and freeze dried overnight to afford anti-3-[4-(2-carboxy-6-hydroxybenzoyl)-3,5-dihydroxybenzoyloxy]-2-(4-hydroxybenzamido)-8-methyl-8-azabicyclo[3.2.1]octane, trifluoroacetic acid salt (120 mg, 82%) as a voluminous pale yellow solid; m.p. 250° C. (dec).

EXAMPLE 12

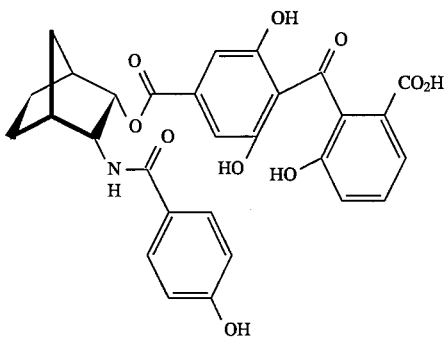

syn-2-[4-(2-Hydroxycarbonyl-6-hydroxybenzoyl)3,5-dihydroxy-benzoyloxy]-3-(4-hydroxybenzamido)bicyclo[2.2.1]heptane To a solution of (±) norcamphor (5.5 g, 50 mmol) in benzene (30 mL) and ether (10 mL) was added isoamyl nitrite (7.45 mL, 55 mmol) at 0° C. under nitrogen. The solution was cooled to −10° C. and sodium tert-butoxide (10 g, 104 mmol) was added portionwise (1 h), keeping the internal temperature at approximately −10° C. After the addition, the reaction mixture was stirred for 1 h at −10° C., then at −5° C. for 12 h. The mixture was poured into ice/water (50 mL) and washed with ether (3×40 mL). The aqueous phase was acidified with 2N HCl and extracted with ether (3×50 mL). The combined organic layers were dried (Na$_2$SO$_4$) and evaporated to give 6.6 g of crude material. Column chromatography (Silica gel; hexane:EtOAc/80:20) afforded 3.7 g of the corresponding oxime (53%) as an oil.

To a solution of the oxime obtained above (600 mg, 4.32 mmol) in ether (20 mL) was added LAH (350 mg, 9.22 mmol) portionwise at room temperature under nitrogen. The reaction mixture was then refluxed for 3.5 h, cooled to room temperature, diluted with ether (20 mL), and carefully added to a solution of Rochelle's salt. The ether layer was separated and the aqueous layer extracted with ether (3×10 mL). The combined solution was dried (Na$_2$SO$_4$) and evaporated to give 450 mg of a white semisolid material (82%). The residue was used directly in the next reaction step without any further purification.

To an ice-cold solution of 2-hydroxy-3-aminobicyclo[2.2.1]heptane (400 mg, 3.14 mmol) in CH$_2$Cl$_2$ (18 mL) was added KOH (2.0M sol, 5 mL). p-Benzyloxybenzoyl chloride (775 mg, 3.14 mmol) was then added portionwise. The reaction mixture was allowed to warm to room temperature and stirred for 2.5 h, then diluted with H$_2$O/CH$_2$Cl$_2$ (1:1, 30 mL) and the organic phase separated. The aqueous layer was extracted with CH$_2$Cl$_2$ (3×20 mL). The combined organic solution was washed with brine, dried (Na$_2$SO$_4$), and evaporated in vacuo. The residue was purified by chromatography (silica gel; hexanes/EtOAc, 60:40) to give 580 mg (55%) of syn-endo-2-hydroxy-3-(4-benzyloxybenzamido)bicyclo[2.2.1]heptane and 20 mg (1.9%) of the corresponding anti-2-hydroxy-3-(4-benzyloxybenzamido)bicyclo[2.2.1]-heptane. Syn: m.p. 158°–160° C.

To a solution of syn-endo-2-hydroxy-3-(4-benzyloxybenzamido)bicyclo[2.2.1]heptane (135 mg, 0.4 mmol) in CH$_2$Cl$_2$ (8 mL) was added DMAP (25 mg), Et3N (0.21 mL, 1.5 mmol), followed by the slow addition of a solution of the corresponding Example 2 acid chloride (ca 0.4 mmol) in CH$_2$Cl$_2$ (4 mL) at room temperature under nitrogen. The reaction mixture was stirred at room temperature for 4 h, then the solvent was partially evaporated in vacuo and the crude mixture purified by flash chromatography (silica gel; hexane/EtOAc, 70:30) to afford 280 mg (70%) of syn-endo-2-[4-(2-benzyloxycarbonyl-6-benzyloxybenzoyl)-3,5-dibenzyloxybenzoyloxy]-3-(4-benzyloxybenzamido)bicyclo[2.2.1]heptane.

To a solution of the coupled material obtained above (280 mg, 280 µmol) in EtOAc/EtOH (3:1, 90 mL) was added 20% Pd(OH)$_2$/C (120 mg). The reaction mixture was then stirred at room temperature under H$_2$ for 3 days. The mixture was filtered through Celite® and the solvent evaporated in vacuo. The yellow residue was purified by HPLC (21×250 mm C$_{18}$ column; A: 5% CH$_3$CN in H$_2$O+0.1% TFA, B: 100% CH$_3$CN; 0–50 B over 1 h) to give 108 mg (67%) of product as a light yellow powder; m.p. 174°–181° C. (dec).

EXAMPLE 13

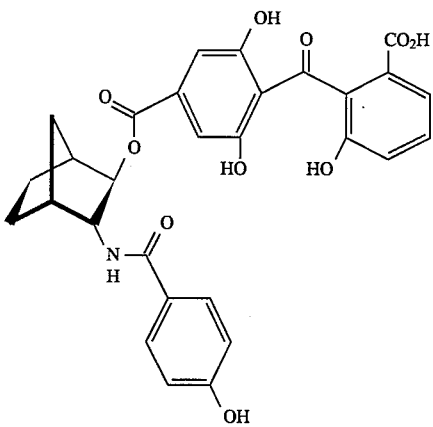

anti-2-[4-(2-Hydroxycarbonyl-6-hydroxy-
benzoyl)-3,5-dihydroxybenzoyloxy]-3-(4-
hydroxybenzamido)bicyclo[2.2.1]heptane To a solution of (±) norcamphor (5.5 g, 50 mmol) in benzene (30 mL) and ether (10 mL) was added isoamyl nitrite (7.45 mL, 55 mmol) at 0° C. under nitrogen. The solution was cooled to −10° C. and sodium tert-butoxide (10 g, 104 mmol) was added portionwise (1 h), keeping the internal temperature at ≈−10° C. After the addition, the reaction mixture was stirred for 1 h at −10° C., then at −5° C. for 12 h. The mixture was poured into ice/water (50 mL) and washed with ether (3×40 mL). The aqueous phase was acidified with 2N HCl and extracted with ether (3×50 mL). The combined organic layers were dried ($Na_2SO_4$) and evaporated to give 6.6 g of crude material. Column chromatography (Silica gel; hexane:EtOAc/80:20) afforded 3.7 g of the corresponding oxime (53%) as an oil.

To a solution of the oxime obtained above (560 mg, 4.02 mmol) in absolute EtOH (25 mL) was added an excess of sodium (until the solution was saturated) portionwise at room temperature. When the reaction was completed as indicated by TLC (hexane:EtOAc/1:1), the solvent was evaporated in vacuo and to the gummy residue was added ether. The white precipitate (sodium ethoxide) was separated by filtration, and the organic phase was washed with brine, dried ($Na_2SO_4$), and evaporated. The crude aminoalcohol (320 mg) was used directly in the next reaction step without any further purification.

To an ice-cold solution of 2-hydroxy-3-aminobicyclo[2.2.1]heptane (320 mg, ca. 2.52 mmol) in dichloromethane (20 mL) was added KOH (2.0M sol, 5 mL). 4-Benzyloxybenzoyl chloride (621 mg, 2.52 mmol) was added portionwise. The reaction mixture was allowed to warm to room temperature and stirred for 2.5 h, then diluted with $H_2O$/$CH_2Cl_2$ (1:1, 30 mL) and the organic phase separated. The aqueous layer was extracted with $CH_2Cl_2$. The organic layer was washed with brine, dried ($Na_2SO_4$), and evaporated in vacuo. The residue was purified by chromatography (silica gel; hexanes/EtOAc, 60:40) to give 170 mg (20%) of syn-endo2-hydroxy-3-(4-benzyloxybenzamido)bicyclo[2.2.1]heptane and 195 mg (23%) of anti-2-hydroxy-3-(4-benzyloxybenzamido)bicyclo[2.2.1]heptane. Anti: m.p. 153°–154° C.

To a solution of anti-2-hydroxy-3-(4-benzyloxybenzamido)bicyclo[2.2.1]heptane (135 mg, 0.4 mmol) in $CH_2Cl_2$ (8 mL) was added DMAP (25 mg), $Et_3N$ (0.21 mL, 1.5 mmol), followed by the slow addition of a solution of the corresponding Example 2 acid chloride (ca 0.4 mmol) in $CH_2Cl_2$ (4 mL) at room temperature under nitrogen. The reaction mixture was stirred at room temperature for 3 h, then the solvent was partially evaporated in vacuo and the crude mixture purified by flash chromatography (silica gel; hexane/EtOAc, 70:30) to afford 295 mg (74%) of anti-2-[4-(2-benzyloxycarbonyl-6-benzyloxybenzoyl)-3,5-dibenzyloxybenzoyloxy]3-(4-benzyloxybenzamido)bicyclo[2.2.1] heptane.

To a solution of the coupled material obtained above (295 mg, 295 µmol) in EtOAc/EtOH (3:1, 21 mL) was added 20% $Pd(OH)_2$/C (120 mg). The reaction mixture was then stirred at room temperature under $H_2$ for 2 days. The mixture was filtered through Celite® and the solvent evaporated in vacuo. The yellow residue was purified by HPLC (21×250 mm $C_{18}$ column; A: 5% $CH_3CN$ in $H_2O$+0.1% TFA, B: 100% $CH_3CN$; 0–50 B over 1 h) to give 110 mg (68%) of product as a light yellow powder; m.p. 185°–193° C. (dec).

EXAMPLE 14

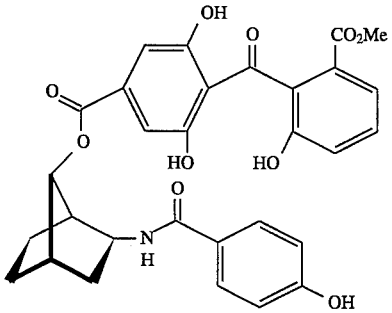

7-[4-(2-Methoxycarbonyl-6-hydroxybenzoyl)-3,5-
dihydroxy-benzoyloxy]-2-(4-
hydroxybenzamido)bicyclo[2.2.1]heptane To a solution of Example 15 acid (28 mg, 51 µmol) in $CH_3OH$ (0.5 mL) was added $TMSCHN_2$ (10% solution in $CH_2Cl_2$, 0.3 ml) dropwise at room temperature under $N_2$. After the addition, the reaction mixture was stirred at room temperature for 30 min, then the solvent was evaporated in vacuo. The residue was purified by preparative TLC (silica gel, $CH_2Cl_2$/ toluene/hexanes/EtOAc/$CH_3OH$, 4:2:1:2:1) to afford a yellow residue which was then triturated with hexanes-$Et_2O$ (1:1) to give 16 mg (55%) of product as a light yellow powder after filtration; m.p. 205°–212° C. (dec).

EXAMPLE 15

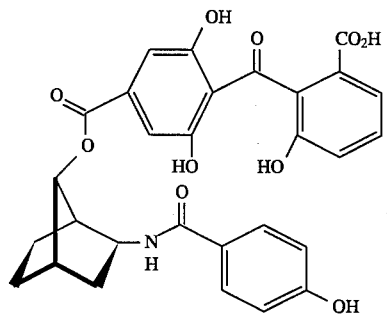

7-[4-(2-Hydroxycarbonyl-6-hydroxy-
benzoyl)-3,5-dihydroxybenzoyloxy]-2-(4-
hydroxybenzamido)bicyclo[2.2.1]heptane To a solution of $Ti(OiPr)_4$ (1.19 ml, 4 mmol) in dichloromethane (15 mL) was added $TMSN_3$ (2.12 mL, 8 mmol) dropwise at 0° C. under nitrogen. The reaction mixture was stirred at 0° C. for 20 min, then a solution of 2,3-exoepoxynorbornane (881 mg, 8 mmol) in dichloromethane (4 mL) was added dropwise at 0° C. The reaction mixture was stirred for 1 h, then it was allowed to warm to room temperature and stirred for 16 h. The solution was passed through a pad of silica gel and the solvent evaporated in vacuo. The yellow residue was purified by column chromatography (silica gel; H:EtOAc/9:1, then 8:2) to give 700 mg (57%) of the corresponding azidoalcohol derivative; m.p. 52°–54° C.

To a solution of the azido compound (256 mg, 1.67 mmol) in EtOAc/EtOH (3:1, 20 mL) was added 10% Pd/C (56 mg). The reaction mixture was then stirred at room temperature under $H_2$ for 18 h. The mixture was filtered through Celite® and the solvent evaporated in vacuo to give 210 mg (99%) of the corresponding aminoalcohol. The crude residue was used directly in the next reaction step without any further purification.

To an ice-cold solution of 2-amino-7-hydroxybicyclo [2.2.1]heptane obtained above (200 mg, 1.57 mmol) in $CH_2Cl_2$ (18 mL) was added KOH (2.0M sol, 4 mL). 4-Benzyloxybenzoyl chloride (387 mg, 1.57 mmol) was then added portionwise. The reaction mixture was allowed to warm to room temperature and stirred for 2.5 h, then diluted with $H_2O/CH_2Cl_2$ (1:1, 20 mL) and the organic phase separated. The aqueous layer was extracted with $CH_2Cl_2$ (3×10 mL). The combined organic solution was washed with brine, dried ($Na_2SO_4$), and evaporated in vacuo. The residue was purified by chromatography (silica gel; hexanes/EtOAc, 60:40 then 1:1) to give 320 mg (60%) of 7-hydroxy-2-(4-benzyloxybenzamido)bicyclo[2.2.1]heptane as a white solid material; m.p. 154°–155° C.

To a solution of 7-hydroxy-2-(4-benzyloxybenzamido)bicyclo[2.2.1]-heptane (135 mg, 0.4 mmol) in $CH_2Cl_2$ (8 mL) was added DMAP (10 mg), $Et_3N$ (0.21 mL, 1.5 mmol), followed by the slow addition of a solution of the corresponding benzophenone acid chloride (ca 0.4 mmol) in $CH_2Cl_2$ (4 mL) at room temperature under nitrogen. The reaction mixture was stirred at room temperature for 3 h, then the solvent was partially removed in vacuo and the crude mixture purified by flash chromatography (silica gel; hexane/EtOAc, 1:1) to afford 200 mg (50%) of 7-[4-(2-benzyloxycarbonyl-6-benzyloxybenzoyl)-3,5-dibenzyloxybenzoyloxy]-2-(4-benzyloxybenzamido)bicyclo[2.2.1]heptane.

To a solution of 7-[4-(2-benzyloxycarbonyl-6-benzyloxybenzoyl)-3,5-dibenzyloxybenzoyloxy]-2-(4-benzyloxybenzamido)bicyclo[2.2.1]heptane (180 mg, 180 μmol) in EtOAc/EtOH (3:1, 21 mL) was added 20% Pd(OH)$_2$/C (100 mg). The reaction mixture was then stirred at room temperature under $H_2$ for 20 h. The mixture was filtered through Celite® and the solvent evaporated in vacuo. The yellow residue was purified by HPLC (21×250 mm $C_{18}$ column; A: 5% $CH_3CN$ in $H_2O$ +0.1% TFA, B: 100% $CH_3CN$; 0–50 B over 1 h) to give 68 mg (69%) of product as a light yellow powder; m.p. 177°–183° C. (dec).

EXAMPLE 16

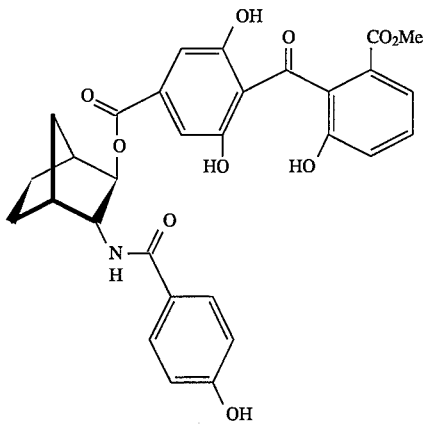

anti-2-[4-(2-Methoxycarbonyl-6-hydroxybenzoyl)-3,5-dihydroxy-benzoyloxy]-3-(4-hydroxybenzamido)bicyclo[2.2.1]heptane To a solution of Example 13 acid (28 mg, 51 μmol) in MeOH (0.5 mL) was added TMSCHN$_2$ (10% solution in $CH_2Cl_2$, 0.3 ml) dropwise (over a period of 1.5 h) at rt under $N_2$. After the reaction was complete as indicated by TLC, MeOH (1 mL) was added and the solvent evaporated in vacuo. The residue was purified by preparative TLC (silica gel, $CH_2Cl_2$/hexanes/-EtOAc/MeOH, 4:3.5:2:0.5) to afford a yellow residue which was then triturated with hexanes-Et$_2$O (1:1) to give 15 mg (53%) of product as a light yellow powder after filtration; m p 185°–191° C. (dec).

EXAMPLE 17

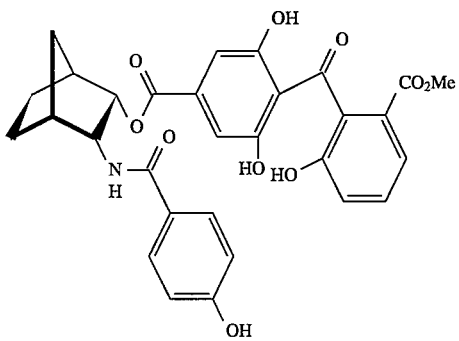

syn-2-[4-(2-Methoxycarbonyl-6-hydroxybenzoyl)-3,5-dihydroxybenzoyl-oxy]-3-(4-hydroxybenzamido)bicyclo[2.2.1]heptane To a solution of the Example 12 acid (55 mg, 0.1 mmol) in MeOH (1 mL) was added TMSCHN$_2$ (2M solution in hexane, 0.5 ml) dropwise (over 3.5 h) at rt under $N_2$. The reaction mixture was stirred for an additional period of 0.5 h after the addition of the solution of TMSCHN$_2$. Methanol (1 mL) was then added and the solvent evaporated in vacuo. The residue was purified by preparative TLC (silica gel, $CH_2Cl_2$/EtOAc/hexane/MeOH, 4:3:2.5:0.5, developed twice) to afford a yellow residue which was then triturated with hexanes-Et$_2$O (1:1) to give 42 mg (75%) of product as a light yellow powder after filtration; m p 162°–170° C. (dec).

EXAMPLE 18

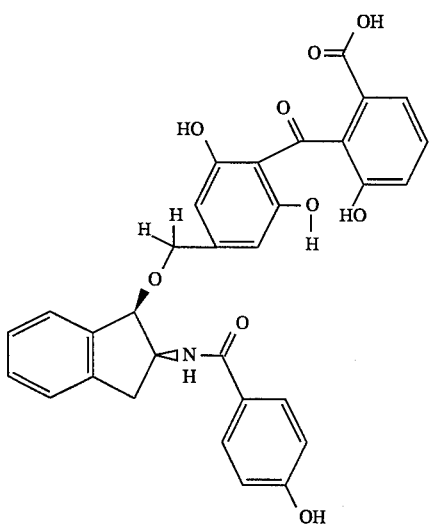

anti-1-[4-(2-Carboxy-6-hydroxybenzoyl)-3,5-dihydroxybenzyloxy]-2-(4-hydroxybenzamido)indane To a solution of 2'-(1,6-dioxanyl)-6'methoxymethoxy-2,6-di(methoxymethoxy)-4-(1,1-dimethylethylsilyloxymethyl)benzophenone (858 mg, 1.45 mmol in anhydrous THF (10 mL) under an atmosphere of nitrogen was added tetrabutylammonium fluoride (2.89 mL, 2,89 mmol, 1M in THF) dropwise over 5 min. The reaction mixture was allowed to stir for 2 h at room temperature, and then was diluted with ethyl acetate (150 mL) and washed with water (2×30 mL) and brine (30 mL). The ethyl acetate layer was dried over anhydrous magnesium sulfate, filtered, and the volatiles were removed under reduced pressure. The crude residue was purified by flash column chromatography (silica gel, 3:1 ethyl acetate: hexane which provided an oil of the alcohol (625 mg, 90%).

To a solution of the alcohol (560 mg, 1.17 mmol) in anhydrous dichloromethane (15 mL) under an atmosphere of nitrogen at 0° C. was added triethylamine (326 mL, 2.34 mmol) and methanesulfonyl chloride (100 mL, 1.29 mmol) dropwise over 10 min. The reaction mixture was allowed to warm to room temperature while stirring over 1 h. The reaction mixture was diluted with ethyl acetate (150 mL) and washed with distilled water (40 mL) and brine (25 mL). The ethyl acetate layer was dried over anhydrous MgSO₄, filtered and the volatiles were removed under reduced pressure.

To a solution of the crude mesylate obtained above in HPLC grade acetone (20 mL) was added sodium iodide (523 mg, 3.51 mmol) under an atmosphere of nitrogen and the reaction mixture was allowed to stir for 2.5 h at room temperature. The reaction mixture was diluted with ethyl acetate (150 mL) and washed with distilled water (50 mL) and brine (30 mL). The ethyl acetate layer was dried over anhydrous MgSO₄, filtered and the volatiles were removed under reduced pressure.

To a suspension of sodium hydride (140 mg, 3.51 mmol, 60% in mineral oil) in freshly distilled anhydrous THF (5 mL) under an atmosphere of nitrogen at 0° C. is added a solution of anti-1-(4-Benzyloxybenzamido)-2-indanol (330 mg, 1.24 mmol) in freshly distilled anhydrous THF (20 mL) dropwise over 15 min. The reaction mixture is allowed to stir while warming to room temperature over 1.5 h. A solution of the above generated iodide in freshly distilled anhydrous THF (20 mL) is added dropwise over 20 min. The reaction mixture is allowed to stir for 3 h at room temperature. The reaction mixture is recooled to 0° C. and quenched with saturated NH₄Cl (10 mL). The reaction mixture is diluted with ethyl acetate (250 mL) and washed with distilled water (75 mL) and brine (25 mL). The ethyl acetate layer is dried over anhydrous MgSO₄, filtered, and the volatiles are removed under reduced pressure. The crude product is purified by flash column chromatography (silica gel, 1% methanol chloroform).

To a suspension of silica gel (1.03 g) in dichloromethane (1.40 mL) was added 2.5% H₂SO₄ (103 mg). The reaction mixture is allowed to stir until the lower layer disappeared. The acetal from the previous step (345 mg, 0.477 mmol) in dichloromethane (10 mL) is added and the reaction mixture is allowed to stir overnight. The reaction mixture is quenched with 1N NaOH (50 mL) and filtered. The volatiles are removed under reduced pressure to provide a crude mixture of two aldehydes.

To a solution of the crude aldehydes in acetonitrile (20 mL) under an atmosphere of nitrogen at 0° C. is added N,N-diisopropylethylamine (166 ml, 0.954 mmol) followed by the dropwise addition of chloromethyl methyl ether (72 mL, 0.954 mmol) over 10 min. The reaction mixture is allowed to stir at room temperature for 48 h during which time additional diisopropylethylamine (966 mL, 5.72 mmol) and chloromethyl methyl ether (432 mL, 5.72 mmol) are added in six portions. The reaction mixture is diluted with ethyl acetate (75 mL) and washed with distilled water (3×25 mL) and brine (1×25 mL). The ethyl acetate layer is dried over MgSO₄, filtered and the volatiles are removed under reduced pressure. The residue is purified by flash column chromatography (silica gel, 100:1 Chloroform: methanol) followed by radial chromatography (silica gel, 200:1 Chloroform: methanol) to provide the title compound. (432 mL,5.72 mmol) are added in six portions. The reaction mixture is diluted with ethyl acetate (75 mL) and washed with distilled water (3×25 mL) and brine (1×25 mL). The ethyl acetate layer is dried over MgSO₄, filtered and the volatiles are removed under reduced pressure. The residue is purified by flash column chromatography (silica gel, 100:1 Chloroform:methanol) followed by radial chromatography (silica gel, 200:1 Chloroform:methanol) to provide the title compound.

anti-1-[4-(2-Carboxy-6-hydroxybenzoyl)-3,5-dihydroxybenzyloxy]-2-(4-hydroxybenzamido)indane To a solution of the aldehyde from the preceding step (142 mg, 0.213 mmol) in acetonitrile (50 mL) is added a solution of sulfamic acid (28 mg, 0.285 mmol) in distilled water (3 mL) dropwise over 5 min followed by the dropwise addition of a solution of NaClO₂ (32 mg, 0.285 mmol) in distilled water (3 mL) over 5 min. After allowing the reaction mixture to stir for 0.5 h at room temperature the volatiles are removed under reduced pressure. The residue is dissolved in ethyl acetate (175 mL) and washed with distilled water (3×20 mL) and brine (1×20 mL). The ethyl acetate layer is dried over anhydrous MgSO₄, filtered, and the volatiles are removed under reduced pressure.

To a solution of crude carboxylic acid (90 mg, 0.132 mmol) in methanol (12 mL) is added conc. HCl (30 drops) at room temperature and the reaction mixture is allowed to stir for 5 h. The volatiles are removed under reduced pressure. The product is chromatographed on a Dynamax®-60 C18 column (21 mm ID×30 cm length) using a linear gradient from 100% A (0.1% TFA and 5% acetonitrile in water) to 100% B (pure acetonitrile) over 60 m at 15 mL/min. Removal of the volatiles under reduced pressure provides the title compound.

EXAMPLE 19 anti-2-[4-(2-Carboxy-6-hydroxybenzoyl)-3,5-dihydroxybenzoyloxy]-3-(4-hydroxybenzamido)bicyclo[2.2.1]-1,7,7-trimethylheptane

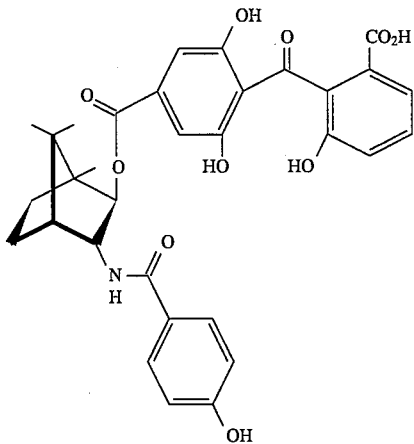

2-hydroxy-3-(4-benzyloxybenzamido)bicyclo[2.2.1]-1,7,7-trimethylheptane

To a solution of (1R)-(+)-camphorquinone-3-oxime (700 mg, 3.86 mmol) in absolute EtOH (20 mL) was added an excess of sodium (until the solution was saturated) portionwise at room temperature. The hot mixture was stirred for 4 h (a small amount of starting material remained). The solvent was evaporated in vacuo. The crude residue was used directly in the next reaction step without any further purification.

To an ice-cold solution of 2-hydroxy-3-aminobicyclo[2.2.1]-1,7,7-trimethylheptane (ca. 3.86 mmol) in dichloromethane (12 mL) was added potassium hydroxide (2.0M sol, 6 mL). 4-Benzyloxybenzoyl chloride (951.5 mg, 3.86 mmol) was added portionwise. The reaction mixture was allowed to warm to room temperature and stirred for 3 h, then diluted with $CH_2Cl_2$ (10 mL) and the organic phase separated. The aqueous layer was extracted with $CH_2Cl_2$ (3×15 mL). The organic layer was dried ($Na_2SO_4$), and evaporated in vacuo. The residue was purified by chromatography (silica gel; hexanes/EtOAc, 70:30) to give 150 mg (10% overall) of 2-hydroxy-3-(4-benzyloxybenzamido)bicyclo[2.2.1]-1,7,7-trimethylheptane. m.p. 55°–58° C. $^1$H-NMR (CDCl$_3$, 300MHz) d: 7.73 (2H, d, J=8.8 Hz), 7.40 (5H, m), 7.01 (2H, d, J=8.8 Hz), 6.30 (1H, br s), 5.12 (2H, s), 4.12 (1H, m), 3.76 (1H, s), 3.38 (1H, d, J=2.0 Hz), 1.92 (1H, t, J=4.1 Hz), 1.66 (2H, m), 1.38 (1H, m), 1.20 (3H, s), 1.11 (1H, m), 0.95 (3H, s), 0.92 (3H, s). IR (KBr): 3361, 2953, 2874, 1624, 1607, 1539, 150 0, 1249, 1176, 1011 cm$^{-1}$. Anal. Calcd. for $C_{24}H_{29}NO_3$: C, 75.96; H, 7.70; N, 3.69. Found: C, 76.05; H, 7.95; N, 3.67.

anti-2-[4-(2-benzyloxycarbonyl-6-benzyloxybenzoyl)-3,5-dibenzyloxybenzoyloxy]-3-(4-benzyloxybenzamido)bicyclo[2.2.1]-1,7,7-trimethylheptane To a solution of anti-2-hydroxy-3-(4-benzyloxybenzamido)bicyclo[2.2.1]-1,7,7-trimethylheptane (110 mg, 0.29 mmol) in $CH_2Cl_2$ (4 mL) was added DMAP (25 mg), Et$_3$N (0.21 mL, 1.5 mmol), followed by the slow addition of a solution of the corresponding benzophenone acid chloride (ca 0.324 mmol) in $CH_2Cl_2$ (4 mL) at room temperature under nitrogen. The reaction mixture was stirred at room temperature overnight, then the solvent was partially evaporated in vacuo and the crude mixture purified by flash chromatography (silica gel; hexane/EtOAc, 70:30) to afford 100 mg (33%) of anti-2-[4-(2-benzyloxycarbonyl-6-benzyloxybenzoyl)-3,5-dibenzyloxybenzoyloxy]-3-(4-benzyloxybenzamido)bicyclo[2.2.1]-1,7,7-trimethylheptane.

To a solution of the above material (100 mg, 96 μmol) in EtOAc/EtOH (3:1, 20 mL) was added 20% Pd(OH)$_2$/C (50 mg). The reaction mixture was then stirred at room temperature under hydrogen for 3 days. The mixture was filtered through Celite® and the solvent evaporated in vacuo. The yellow residue was purified by HPLC (21×250 mm C$_{18}$ column; A: 5% CH$_3$CN in H$_2$O+0.1% TFA, B: 100% CH$_3$CN; 0–100 B over 1 h) to give 26 mg (46%) of product as a light yellow powder. m.p. 192°–196° C. dec. $^1$H-NMR (CD$_3$OD, 300MHz) d: 7.53 (2H, d, J=8.7 Hz), 7.28 (1H, d, J=8.2 Hz), 7.06 (1H, t, J=8.1 Hz), 6.81 (1H, d, J=8.1 Hz), 6.70 (2H, s), 6.61 (2H, d, J=8.7 Hz), 4.79 (1H, d, J=3.5 Hz), 4.41 (1H, m), 1.89 (1H, br s), 1.56–1.21 (4H, m), 1.07 (3H, s), 0.76 (3H, s), 0.71 (3H, s). IR (KBr): 3387, 3308, 2961, 1703, 1634, 1607, 1505, 1425, 1368, 1238, 1176, 764 cm$^{-1}$. MS m/e (rel intensity) 590 (M$^+$+1, 32), 589 (M$^+$, 2), 301 (10), 273 (18), 272 (100), 177 (14), 152 (12), 121 (58). Anal. Calcd. for $C_{32}H_{31}NO_{10}$·0.5 TFA: C, 61.30; H, 4.91; N, 2.17. Found: C, 61.50; H, 4.79; N, 2.24.

EXAMPLE 20

8-exo-[4-(2-Carboxy-6-hydroxybenzoyl)-3,5-dihydroxybenzoyloxy]-9-endo-(4-hydroxybenzamido)tricyclo-[5.2.1.0 (2,6)]decane Tricyclo[5.2.1.0 (2,6)]decan-8,9-dione, oxime A cooled (−20° C.) solution of 8-ketotricyclo[5.2.1.0]decane (7.51 g, 50 mmol) in anhydrous tetrahydrofuran (50 mL) under nitrogen was treated with n-butyl nitrite (6.70 mL, 5.92 g, 57.3 mmol), then with solid potassium t-butoxide (11.22 g, 100 mmol) in portions at a rate to keep the pot temperature below −10° C. The red mixture was stirred at −10° C. for one h. and at 5° C. for 3.5 h, then it was quenched by addition to ice water (125 mL). The mixture was treated with concentrated hydrochloric acid (11 mL, 132 mmol), then the aqueous solution was extracted with methylene chloride (150 mL, then 2×100 mL). The combined organic solution was washed with saturated aqueous sodium bicarbonate (2×100 mL), water (100 mL), dried (Na$_2$SO$_4$), and concentrated in vacuo. The residue was chromatographed on silica gel (eluted with 5% acetone/methylene chloride) to afford tricyclo[5.2.1.0 (2,6)]decan-8,9-dione, oxime (4.88 g, 54.5%) as a white solid.

8-exo-Hydroxy-9-endo-(4-phenylmethoxybenzamido)-tricyclo-[5.2.1.0 (2,6)]decane

A solution of tricyclo[5.2.1.0 (2,6)]decan-8,9-dione, oxime (0.90 g, 5.0 mmol) in anhydrous 3A denatured alcohol (50 mL) under nitrogen was treated in portions with sodium spheres (4.0 g, 174 mmol) over 30 min at a rate to keep the temperature between 40°–60° C. The last few spheres did not readily dissolve, and the mixture was heated to 65°±5° C. for one h and concentrated in vacuo. The residue was taken up in toluene (125 mL), then brine (50 mL) and isopropanol (25 mL) were added. The organic layer was separated after shaking, and the aqueous solution was extracted with methylene chloride (2×50 mL) containing some isopropanol. The combined organic solution containing aminoalcohol intermediate was dried (Na$_2$SO$_4$) and concentrated in vacuo. The residue was dissolved in toluene and reconcentrated to ensure that all alcohols were removed, then dissolved in methylene chloride (25 mL) and treated with 1N sodium hydroxide (15 mL) and 4-benzyloxybenzoyl chloride (1.60 g, 6.5 mmol). This mixture was stirred for 18 h and separated. The aqueous solution was extracted with methylene chloride (25 mL), and the combined organic solution was concentrated in vacuo and taken up in 4:1 methanol/water (25 mL). The mixture was treated with potassium hydroxide (2.5 g) and stirred at 55°–60° C. for 2 h, then concentrated to remove most of the methanol. The aqueous solution was extracted with methylene chloride (3×50 mL), and the combined organic solution was washed with water (50 mL), dried ($Na_2SO_4$), and concentrated in vacuo. The residue was chromatographed on silica gel (eluted with 10% acetone/methylene chloride) to afford 8-exo-hydroxy-9-endo(4-phenylmethoxybenzamido)tricyclo[5.2.1.0 (2,6)]decane (0.63 g, 33%), which had mp (EtOAc/hexane) 162°–164° C., and was preceded by the endo-endo isomer (0.26 g, 14%).

8-exo-[4-(2-Carbophenylmethoxy-6-phenylmethoxybenzoyl)-3,5-bis(phenylmethoxy)benzoyloxy]-9-endo-(4-phenylmethoxybenzamido)tricyclo[5.2.1.0 (2,6)]decane A solution of 4-(2-carbophenylmethoxy-6-phenylmethoxybenzoyl)-3,5-bis(phenylmethoxy)benzoic acid (0.34 g, 0.50 mmol) in anhydrous methylene chloride (3 mL) was treated with anhydrous N,N-dimethylformamide (4 drops), then with 2.0N oxalyl chloride/methylene chloride (0.40 mL, 0.80 mmol), and the mixture was stirred for one h under a drying tube. The solution was concentrated in vacuo, diluted with anhydrous toluene (10 mL), reconcentrated in vacuo, and placed under high vacuum for one h. Anhydrous tetrahydrofuran (1.5 mL), anhydrous N,N-dimethylformamide (0.75 mL), triethylamine (0.75 mL), and 4-dimethylaminopyridine (50 mg) were added to the flask, followed closely by 8-exo-hydroxy-9-endo-(4-phenylmethoxybenzamido)tricyclo-[5.2.1.0 (2,6)]decane (0.17 g, 0.45 mmol). The solution was stirred under nitrogen at room temperature for 18 h, then diluted with toluene (25 mL). The organic solution was washed with 0.5N sodium hydroxide (12 mL), water (12 mL), dried ($Na_2SO_4$), and concentrated in vacuo. Silica gel chromatography (eluted with 2% acetone/methylene chloride) afforded 8-exo-[4-(2 -carbophenylmethoxy-6-phenylmethoxybenzoyl)-3,5-bis(phenylmethoxy)-benzoyloxy]-9-endo-(4-phenylmethoxybenzamido)tricyclo-[5.2.1.0 (2,6)]decane (0.332 g, 71%) as a white foam.

8-exo-[4-(2-Carboxy-6-hydroxybenzoyl)-3,5-dihydroxybenzoyloxy]-9-endo-(4-hydroxybenzamido)tricyclo[5.2.1.0 (2,6)]decane A solution of 8-exo-[4-(2-carbophenylmethoxy-6-phenylmethoxybenzoyl)-3,5-bis(phenylmethoxy)benzoyloxy]-9-endo-(4-phenylmethoxybenzamido)tricyclo[5.2.1.0 (2,6)]decane (0.33 g, 0.32 mmol) in 6:1 ethanol/ethyl acetate (50 mL) in a 500 mL Parr bottle was treated with trifluoroacetic acid (0.15 mL) and purged with nitrogen. Pearlman's catalyst (150 mg) was added, and the vessel was charged with hydrogen (50 psi) and shaken on a Parr apparatus for 18 h. The bottle was carefully evacuated of hydrogen and the solution was filtered through Celite®, then the filter cake was washed with ethanol, but not allowed to dry. The filtrate was concentrated in vacuo to a foamy yellow solid, which was dissolved in DMF (0.8 mL) and loaded onto HPLC; conditions: A- 0.1% TFA/5% $CH_3CN/H_2O$, B- $CH_3CN$, 100% A to 100% B over one h, 25 mL/min, 41×250 mm C18 column. Fractions (one/min) 41–44 were combined, partially concentrated in vacuo, treated with some $CH_3CN$ for solubility (product not water-soluble), and freeze-dried over 18 h to afford 8-exo-[4-(2-carboxy-6-hydroxybenzoyl)-3,5-dihydroxy-benzoyloxy]-9-endo-(4-hydroxybenzamido)-tricyclo[5.2.1.0 (2,6)]decane (166 mg, 82%) as a pale yellow voluminous solid; mp 195°–200° C. (dec). $R_f$ (2:1 methylene chloride/methanol on silica) 0.50; IR (KBr) 1703, 1635, 1608 $cm^{-1}$; $^1H$ NMR ($d_6$-DMSO) d 11.66 (s, 2H), 9.97 (br s, 1H), 9.88 (s, 1H), 8.35 (d, 1H, J=7 Hz), 7.75 (d, 2H, J=9 Hz), 7.38 (d, 1H, J=8 Hz), 7.28 (t, 1H, J=8 Hz), 7.06 (d, 1H, J=8 Hz), 6.83 (s, 2H), 6.79 (d, 2H, J=9 Hz), 4.83 (d, 1H, J=2.5 Hz), 4.11 (m, 1H), 2.25 (d, 1H, J=4 Hz), 2.10–2.20 (m, 1H), 2.07 (br s, 2H), 1.60–2.00 (m, 3H), 1.48 (br s, 2H), 1.10–1.30 (m, 1H), 0.90–1.10 (m, 2H); mass spectrum (FAB): m/z 588. Anal. Calcd. for $C_{32}H_{29}NO_{10}·0.25 C_2HF_3O_2·H_2O$: C, 61.56; H, 4.97; N, 2.21. Found: C, 61.39; H, 4.89; N, 2.29.

EXAMPLE 21

8-endo-[4-(2-Carboxy-6-hydroxybenzoyl)-3,5-dihydroxybenzoyl-oxy]-9-endo-(4-hydroxybenzamido)tricyclo[5.2.1.0 (2,6)]decane Tricyclo[5,2,1.0 (2,6)]decan-8,9-dione, oxime A cooled (−20° C.) solution of 8-ketotricyclo[5.2.1.0]decane (7.51 g, 50 mmol) in anhydrous tetrahydrofuran (50 mL) under nitrogen was treated with n-butyl nitrite (6.70 mL, 5.92 g, 57.3 mmol), then with solid potassium t-butoxide (11.22 g, 100 mmol) in portions at a rate to keep the pot temperature below −10° C. The red mixture was stirred at −10° C. for one h and at 5° C. for 3.5 h, then it was quenched by addition to ice water (125 mL). The mixture was treated with concentrated hydrochloric acid (11 mL, 132 mmol), then the aqueous solution was extracted with methylene chloride (150 mL, then 2×100 mL). The combined organic solution was washed with saturated aqueous sodium bicarbonate (2×100 mL), water (100 mL), dried ($Na_2SO_4$), and concentrated in vacuo. The residue was chromatographed on silica gel (eluted with 5% acetone/methylene chloride) to afford tricyclo[5.2.1.0 (2,6)]decan-8,9-dione, oxime (4.88 g, 54.5%) as a white solid.

8-endo-Hydroxy-9-endo-(4-phenylmethoxybenzamido) tricyclo-[5.2.1.0 (2,6)]decane

A solution of tricyclo[5.2.1.0 (2,6)]decan-8,9-dione, oxime (0.90 g, 5.0 mmol) in anhydrous 3A denatured alcohol (50 mL) under nitrogen was treated in portions with sodium spheres (4.0 g, 174 mmol) over 30 min at a rate to keep the temperature between 40°–60° C. The last few spheres did not readily dissolve, and the mixture was heated to 65°±5° C. for one h and concentrated in vacuo. The residue was taken up in toluene (125 mL), then brine (50 mL) and isopropanol (25 mL) were added. The organic layer was separated after shaking, and the aqueous solution was extracted with methylene chloride (2×50 mL) containing some isopropanol. The combined organic solution containing aminoalcohol intermediate was dried ($Na_2SO_4$) and concentrated in vacuo. The residue was dissolved in toluene and reconcentrated to ensure that all alcohols were removed, then dissolved in methylene chloride (25 mL) and treated with 1N sodium hydroxide (15 mL) and 4-benzyloxybenzoyl chloride (1.60 g, 6.5 mmol). This mixture was stirred for 18 h and separated. The aqueous solution was extracted with methylene chloride (25 mL), and the combined organic solution was concentrated in vacuo and taken up in 4:1 methanol/water (25 mL). The mixture was treated with potassium hydroxide (2.5 g) and stirred at 55°–60° C. for 2 h, then concentrated to remove most of the methanol. The aqueous solution was extracted with methylene chloride (3×50 mL), and the combined organic solution was washed with water (50 mL), dried ($Na_2SO_4$), and concentrated in vacuo. The residue was chromatographed on silica gel (eluted with 10% acetone/methylene chloride) to afford 8-endo-hydroxy-9-endo-(4-phenylmethoxybenzamido)tricyclo[5.2.1.0 (2,6)]decane (0.26 g, 14%), which had mp (acetonitrile) 174°–179° C., and was followed by the exo-endo isomer (0.63 g, 33%).

8-endo-[4-(2-Carbophenylmethoxy-6-phenylmethoxybenzoyl)3,5-bis(phenylmethoxy)benzoyloxy]-9-endo-(4-phenylmethoxy-benzamido)tricyclo[5.2.1.0. (2,6)]decane A solution of 4-(2-carbophenylmethoxy-6-phenylmethoxybenzoyl)-3,5-bis(phenylmethoxy)benzoic acid (0.20 g, 0.29 mmol) in anhydrous methylene chloride (2 mL) was treated with anhydrous N,N-dimethylformamide (3 drops), then with 2.0N oxalyl chloride/methylene chloride (0.20 mL, 0.40 mmol), and the mixture was stirred for one h under a drying tube. The solution was concentrated in vacuo, diluted with anhydrous toluene (10 mL), reconcentrated in vacuo, and placed under high vacuum for one h. Anhydrous tetrahydrofuran (1.0 mL), anhydrous N,N-dimethylform-amide (0.4 mL), triethylamine (0.4 mL), and 4-dimethylaminopyridine (30 mg) were added to the flask, followed closely by 8-endo-hydroxy-9-endo-(4-phenylmethoxybenzamido)tricyclo[5.2.1.0 (2,6)]decane (0.087 g, 0.23 mmol). The solution was stirred under nitrogen at room temperature for 18 h, then diluted with toluene (20 mL). The organic solution was washed with 0.5N sodium hydroxide (10 mL), water (10 mL), dried ($Na_2SO_4$), and concentrated in vacuo. Silica gel chromatography (eluted with 5% acetone/methylene chloride) afforded 8-endo-[4-(2-carbophenylmethoxy-6-phenylmethoxybenzoyl)-3,5-bis(phenylmethoxy)benzoyloxy]-9-endo-(4-phenylmethoxybenzamido)tricyclo-[5.2.1.0 (2,6)] decane (0.226 g, 94%) as a white foam.

8-endo-[4-(2-Carboxy-6-hydroxybenzoyl)-3,5-dihydroxybenzoyl-oxy]-9-endo-(4-hydroxybenzamido) tricyclo-[5.2.1.0 (2,6)]decane A solution of 8-endo-[4-(2-carbophenylmethoxy-6-phenylmethoxybenzoyl-3,5-bis(phenylmethoxy)benzoyloxy]-9-endo-(4-phenylmethoxybenzamido)-tricyclo[5.2.1.0 (2,6)]decane (0.22 g, 0.21 mmol) in 4:1 ethanol/ethyl acetate (25 mL) in a 500 mL Parr bottle was treated with trifluoroacetic acid (0.10 mL) and purged with nitrogen. Pearlman's catalyst (120 mg) was added, and the vessel was charged with hydrogen (50 psi) and shaken on a Parr apparatus for 18 h. The bottle was carefully evacuated of hydrogen and the solution was filtered through Celite®, then the filter cake was washed with ethanol, but not allowed to dry. The filtrate was concentrated in vacuo to a foamy yellow solid, which was dissolved in DMF (0.6 mL) and loaded onto HPLC; conditions: A- 0.1% TFA/5% $CH_3CN/H_2O$, B- $CH_3CN$, 100% A to 100% B over one h, 25 mL/min, 41×250 mm C18 column. Fractions (one/min) 42–44 were combined, partially concentrated in vacuo, treated with some $CH_3CN$ for solubility (product not water-soluble), and freeze-dried over 18 h to afford 8-endo-[4-(2-carboxy-6-hydroxybenzamido)-3,5-dihydroxy-benzoyloxy]-9-endo-(4-hydroxybenzamido)-tricyclo[5.2.1.0 (2,6)]decane (93.2 mg, 70%) as a pale yellow voluminous solid; mp 184°–189° C. $R_f$ (15% methanol/methylene chloride on silica) 0.25; IR (KBr) 1709, 1634, 1608 cm$^{-1}$; $^1$H NMR (d$_6$-DMSO) d 11.67 (s, 2H), 9.87 (br s, 2H), 7.63 (d, 2H, J=9 Hz), 7.60 (m, 1H), 7.38 (d, 1H, J =8 Hz), 7.29 (t, 1H, J=8 Hz), 7.06 (d, 1H, J=8 Hz), 6.95 (s, 2H), 6.72 (d, 2H, J=9 Hz), 5.15 (dd, 1H, J=10, 4.5 Hz); 4.47 (m, 1H), 2.40–2.65 (m, 2H), 2.36 (d, 1H, J=4 Hz), 2.12 (d, 1H, J=4 Hz), 1.85 (m, 2H), 1.65 (m, 1H), 1.51 (d, 1H, J=11 Hz), 1.28 (d, 1H, J=11 Hz), 1.20 (m, 1H), 1.00 (m, 2H); mass spectrum (FAB): m/z 588. Anal. Calcd. for $C_{32}H_{29}NO_{10}.0.25C_2HF_3O_2.0.5H_2O$: C, 62.45; H, 4.88; N, 2.24. Found: C, 62.30; H, 4.86; N, 2.26

EXAMPLE 22

An oral dosage form for administering the presently invented compounds is produced by screening, mixing, and filling into a hard gelatin capsule the ingredients in Table 2 below.

TABLE 2

| Ingredients | Amounts |
|---|---|
| syn-3-[4-(2-Carboxy-6-hydroxybenzoyl)-3,5-dihydroxybenzoyloxy]-2-(4-hydroxybenzamido)-8-methyl-8-azabicyclo[3.2.1]octane | 50 mg |
| magnesium stearate | 5 mg |
| lactose | 75 mg |

EXAMPLE 23

The sucrose, calcium sulfate dihydrate and pyridylimidazole shown in Table 3 below, are mixed and granulated with a 10% gelatin solution. The wet granules are screened, dried, mixed with the starch, talc and stearic acid, screened and compressed into a tablet.

TABLE 3

| Ingredients | Amounts |
|---|---|
| syn-2-[4-(2-Hydroxycarbonyl-6-hydroxybenzoyl)-3,5-dihydroxybenzoyloxy]-3-(4-hydroxybenzamido)-bicyclo[2.2.1]heptane | 100 mg |
| calcium sulfate dihydrate | 150 mg |
| sucrose | 20 mg |
| starch | 10 mg |
| talc | 5 mg |

EXAMPLE 24

Syn-4-[4-(2-Carboxy-6-hydroxybenzoyl)-3,5-dihydroxybenzoyloxy]-3-(4-hydroxybenzoylamino)-1-azabicyclo [3.2.2]nonan trifluoroacetic acid salt, 75 mg, is dispersed in 25 ml of normal saline to prepare an injectable preparation.

While the preferred embodiments of the invention are illustrated by the above, it is to be understood that the invention is not limited to the precise instructions disclosed herein and that the exclusive right to all modifications within the scope of the following claims and all equivalents thereof is reserved.

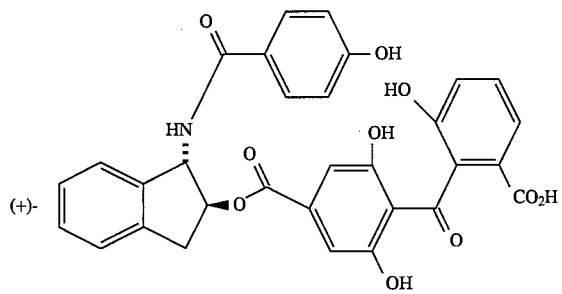

(+)-anti-1-(4-Hydroxybenzamido)-2-[3,5-dihydroxy-4-(2-carboxy-6-hydroxybenzoyl)benzoyloxy]indane (+)-1-(4-Benzyloxy)benzamido-2-[α-methoxy-α-(trifluoromethyl)phenyl]acetyloxyindane To a suspension of 1-(4-benzyloxy)benzamido-2-hydroxyindane (500 mg, 1.39 mmol), triethylamine (352 mg, 484 ml, 3.48 mmol), and DMAP (169 mg, 1.39 mmol) in $CH_2Cl_2$ (15 mL) was added dropwise (S)-(+)-α-methoxy- α-(trifluoromethyl)phenylacetyl chloride (404 mg, 300 ml, 1.60 mmol) at room temperature. After stirring at rt for 1 h, the reaction mixture was chromatographed eluting with 2.5:1/Hexane:EtOAc to generate a clear pale yellow oil (760 mg, 95%). Recrystallization of the oil from MeOH yielded a single enantiomer (140 mg, >99% ee determined from $^1$Hnmr and analytic HPLC).

(+)-1-(4-Benzyloxy)benzamido-2-hydroxyindane

To a solution of 1-(4-benzyloxy)benzamido-2-[α-methoxy-α-(trifluoromethyl)phenyl]acetyloxyindane (132 mg, 0.23 mmol) in EtOH-THF (3:1, 4 mL) was added a solution of KOH (515 mg, 9.20 mmol) in water (1 mL). The mixture was stirred at rt for 4 h. The white solid, which precipitated from reaction mixture, was collected, rinsed with EtOH, and dried in a vacuum oven (67 mg, 82%).

(+)-1-(4-Benzyloxybenzamido)-2-[3,5-dibenzyloxy-4-(2benzyloxycarbonyl-6-benzyloxybenzoyl)benzoyloxy]indane To a solution of 4-(6-benzyloxy-2-(benzyloxycarbonyl)benzoyl)-3,5-dibenzyloxybenzoic acid (122 mg, 0,179 mmol) in CH$_2$Cl$_2$ (3 mL) was added cat. DMF and oxalyl chloride (2.0M solution in CH$_2$Cl$_2$, 224 mL, 0.448 mmol) at rt. The mixture was stirred at rt for 2 h and solvents were removed, then the acid chloride residue was taken up into CH$_2$Cl$_2$ (5 mL) after vacuum drying for 1 h. A solution of 1-(4-benzyloxy)benzamido-2-hydroxyindane (56 mg, 0.156 mmol), Et$_3$N (78.8 mg, 109 mL, 0.780 mmol) and DMAP (19.0 mg, 0.156 mmol) in CH$_2$Cl$_2$ (5 mL) was treated with the freshly made acid chloride-CH$_2$Cl$_2$ solution at 5° C. The reaction mixture was allowed to stir at rt for 3 h before chromatography on silica gel eluting with 2:1/hexane:EtOAc. The product was obtained as a clear oil (147 mg, 92%).

(+)-anti-1-(4-Hydroxybenzamido)-2-[3,5-dihydroxy-4-(2-carboxy-6-hydroxybenzoyl)benzoyloxy]indane 1-(4-Benzyloxybenzamido)-2-[3,5-dibenzyloxy-4-(2-benzyloxycarbonyl-6-benzyloxybenzoyl)benzoyloxy]-indane (135 mg, 0,130 mmol) was dissolved in EtOAc-HOEt (2:1, 15 mL) and treated with 20% Pd(OH)$_2$/C (63 mg, 45 mol %). The mixture was subject to hydrogenolysis at 50 psi for 18 h. Solvents were removed in vacuo and the residue taken up into MeOH. The resulting MeOH solution was concentrated after filtration through a pad of celite, and the residue was chromatographed on a short silica gel column, eluting with 4:1/EtOAc: Hexane+0.5% HOAc. The title compound was obtained as yellow solids (51.4 mg, 70%); m.p. 174°–176 (dec)° C.; [α]$_{20}$=+181 (c=0.23, MeOH).

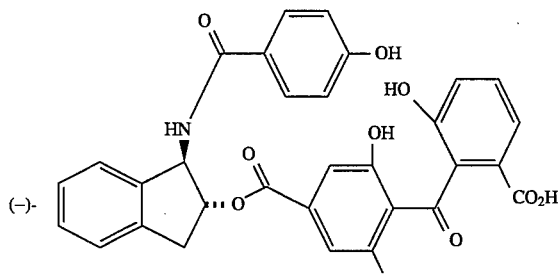

(–)-anti-1-(4-Hydroxybenzamido)-2-[3,5-dihydroxy-4-(2-carboxy-6-hydroxybenzoyl)benzoyloxy]indane (–)-1-(4-Benzyloxy)benzamido-2-[α-methoxy-α-(trifluoromethyl)phenyl]acetyloxyindane To a suspension of 1-(4-benzyloxy)benzamido-2-hydroxyindane (500 mg, 1.39 mmol), triethylamine (352 mg, 484 ml, 3.48 mmol), and DMAP (169 mg, 1.39 mmol) in CH$_2$Cl$_2$ (15 mL) was added dropwise (S)-(+)-α-methoxy-α-(trifluoromethyl)phenylacetyl chloride (404 mg, 300 ml, 1.60 mmol) at room temperature. After stirring for 1 h, the reaction mixture was chromatographed eluting with 2.5:1/Hexane:EtOAc to generate a clear pale yellow oil (760 mg, 95%). Recrystallization of the oil from MeOH yielded a single (+)-enantiomer (140 mg, >99% ee determined from $^1$Hnmr and analytic HPLC) and a mother liquid. Column chromatography of the mother liquid eluting with 2% EtOAC in toluene afforded another single (–)-enantiomer (220 mg, >99% ee determined from $^1$Hnmr and analytic HPLC).

(–)-1-(4-Benzyloxy)benzamido-2-hydroxyindane

To a solution of (–)-1-(4-benzyloxy)benzamido-2-[α-methoxy-α-(trifluoromethyl)phenyl]acetyloxyindane (220 mg, 0.38 mmol) in EtOH-THF (3:1, 6.7 mL) was added a solution of KOH (856 mg, 15.3 mmol) in water (1.7 mL). The mixture was stirred at rt for 4 h. A white solid, which precipitated from reaction mixture, was collected, rinsed with EtOH, and dried in a vacuum oven (95 mg, 70%). Some product was still in the mother liquid.

(–)-1-(4-Benzyloxybenzamido)-2-[3,5-dibenzyloxy-4-(2-benzyloxycarbonyl-6-benzyloxybenzoyl)benzoyloxy]indane To a solution of 4-(6-benzyloxy-2-(benzyloxycarbonyl)benzoyl)-3,5-dibenzyloxybenzoic acid (196 mg, 0.290 mmol) in CH$_2$Cl$_2$ (3 mL) was added cat. DMF and oxalyl chloride (2.0M solution in CH$_2$Cl$_2$, 360 mL, 0.720 mmol) at rt. The mixture was stirred for 2 h, then solvents were removed and the acid chloride residue was taken up into CH$_2$Cl$_2$ (5 mL) after drying under vacuum for 1 h. A solution of (–)-1-(4-benzyloxy)benzamido-2-hydroxyindane (90 mg, 0.250 mmol), Et$_3$N (127 mg, 176 mL, 1.25 mmol) and DMAP (30.6 mg, 0.250 mmol) in CH$_2$Cl$_2$ (5 mL) was treated with the freshly made acid chloride-CH$_2$Cl$_2$solution at 5° C. The reaction mixture was allowed to stir at rt for 3 h before chromatography on silica gel eluting with 2:1/hexane:EtOAc. The product was obtained as a white solid (237 mg, 93%).

(–)-anti-1-(4-Hydroxybenzamido)-2-[3,5-dihydroxy-4-(2-carboxy-6-hydroxybenzoyl)benzoyloxy]indane 1-(4 Benzyloxybenzamido)-2-[3,5-dibenzyloxy-4-(2-benzyloxycarbonyl-6-benzyloxybenzoyl)benzoyloxy]indane (225 mg, 0.220 mmol) was dissolved in EtOAc-HOEt (2:1, 22 mL) and treated with 20% Pd(OH)$_2$/C (106 mg, 45 mol %). The mixture was subjected to hydrogenolysis at 50 psi for 18 h. Solvents were removed in vacuo and the residue taken into MeOH, and the resulting MeOH solution was concentrated after filtration through a pad of celite®. The residue was chromatographed on a short silica gel column, eluting with 4:1/EtOAc: Hexane+0.5% HOAc. The title compound was obtained as yellow solids (107 mg, 85%); m.p. 172°–174 (dec)° C.; [α]$_{20}$=–187 (c=0.23, MeOH).

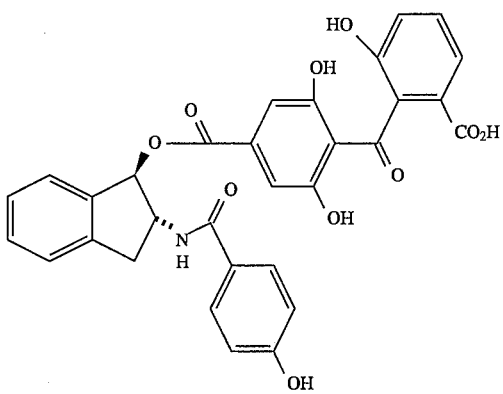

anti-1-[4-(2-Carboxy-6-hydroxybenzoyl)-3,5-
dihydroxybenzoyloxy]-2-(4-hydroxybenzamido)indane syn-2-Amino-1-indanol syn-2-Amino-1-indanol was prepared from the commercially available anti-2-bromo-1-indanol in a quantitative yield by a literature method (Tetrahedron Lett. 1993, 34, 8399–8402).

anti-2-(4-Methoxymethoxybenzamido)-1-indanol

To a solution of $Et_3N$ (903 mg, 1.24 mL, 8.92 mmol) and diethyl phosphorocyanidate (1.16 g, 1.08 mL, 7.14 mmol) in DMF (15 mL) was added 4-methoxymethoxybenzoic acid (650 mg, 3.57 mmol, made from 4-hydroxybenzoic acid). After reaction at rt for 1.5 h, a solution of 2-amino-1-indanol (1.07 g, 7.14 mmol) in DMF (10 mL) was added. The reaction mixture was stirred at rt for overnight, poured into water, and extracted with EtOAc (3×50 mL). The organic layer was washed with brine, dried ($Na_2SO_4$), and chromatographed (silica gel, EtOAc:Hexane/2:3) to afford a mixture of monoacylated compound (syn-2-(4-methoxymethoxybenzamido)-1-indanol, 360 mg, 32%) and bisacylated compound (360 mg, 21%). The latter was saponified with KOH (2N, 10 mL, MeOH:THF/1:1, 20 mL) to generate an additional 205 mg of the title compound (565 mg in total, 50%).

2-(4-Methoxymethoxybenzamido)-1-indanone

To a solution of syn-2-(4-methoxymethoxybenzamido)-1-indanol (500 mg, 1.60 mmol) in acetone (125 mL) was added Jones reagent (3.5 mL) at rt until the wine color of the reaction mixture was maintained for 30 min. Acetone was removed in vacuo and the residue was subjected to an extractive work-up to provide 2-(4-methoxymethoxybenzamido)-1-indanone as a white solid (498 mg, quant.).

anti-2-(4-Methoxymethoxybenzamido)-1-indanol

To an ice-cooled solution/suspension of 2-(4-methoxymethoxybenzamido)-1-indanone (475 mg, 1.5 mmol) in methanol (100 mL) was added $NaBH_4$ (13.9 mg, 3.75 mmol) portionwise. After reaction at rt for 15 min, volatiles were removed in vacuo and the residue triturated in MeOH to afford exclusively trans-2-(4-methoxymethoxybenzamido)-1-indanol as a white solid (279 mg). The mother liquid was chromatographed (silica gel, Hexane:EtOAc/7:1 to 1:1) to afford an additional 82 mg of the product (360 mg in total, 75%).

anti-2-(4-Methoxymethoxybenzamido)-1-[4-[2-methoxymethoxy-6-(1,6-dioxanyl)benzoyl]-3,5-dimethoxymethoxybenzoyloxy]indane A mixture of 3,5-di(methoxymethoxy)-4-[2-(methoxymethoxy)-6-(1,6-dioxanyl)benzoyl]benzoic acid (596 mg, 1.21 mmol) and 1,1-carbonyldiimidazole (222 mg, 1.37 mmol) in DMF (2 mL) was stirred at rt under $N_2$ for 2 h prior to the addition of anti-2-(4-methoxymethoxybenzamido)-1-indanol (330 mg, 1.05 mmol) and 1,8-diazabicyclo[5.4.0]undec-7-ene(192 mg, 189 mmL, 1.26 mmol). After overnight stirring at rt, the reaction mixture was poured into water, extracted with EtOAc, and chromatographed (silica gel, EtOAc:Hexane/1:1) to provide anti-2-(4-methoxymethoxybenzamido)-1-[4-[2-methoxymethoxy -6-(1,6 -dioxanyl)benzoyl]-3,5-dimethoxymethoxybenzoyloxy]indane as a white solid (799 mg, 97%).

anti-2-(4-Methoxymethoxybenzamido)-1-[4-[2-methoxymethoxy-6-(formyl)benzoyl]-3,5-dimethoxymethoxybenzoyloxy]indane To a slurry of silica gel (1.59 g) in $CH_2Cl_2$ (15 mL) was added 15% $H_2SO_4$ (156 mg). The mixture was stirred until the water had been absorbed onto silica gel, and a solution of anti-2-(4-methoxymethoxybenzamido)-1-[4-[2-methoxymethoxy-6-(1,6-dioxanyl)benzoyl]-3,5-dimethoxymethoxybenzoyloxy]indane (570 mg, 0.72 mmol) in $CH_2Cl_2$ (3.5 mL) was added. The resulting mixture was stirred at rt for 6 h. The silica gel was removed by filtration and rinsed with 1% $MeOH/CH_2Cl_2$. The filtrate was chromatographed following concentration (silica gel, EtOAc:Hexane/1:2) to provide the corresponding aldehyde as a white solid (241 mg, 43%).

anti-2-(4-Methoxymethoxybenzamido)-1-[4-[2-methoxymethoxy-6-carboxy)benzoyl]-3,5-dimethoxymethoxybenzoyloxy]indane To a solution of anti-2-(4-methoxymethoxybenzamido)-1-[4-[2-methoxymethoxy-6-(formyl)benzoyl]-3,5-dimethoxymethoxybenzoyloxy]indane (50 mg, 0.07 mmol) in $CH_3CN$ (15 mL) was added a solution of sulfamic acid (9.0 mg, 0.09 mmol) in distl. water (0.93 mL), followed by a solution of $NaClO_2$ (10.3 mg, 0.09 mmol) in distl. water (0.93 mL) at rt. Volatiles were removed in vacuo after 30 min, and the white solids were used for the next reaction (deprotection) without further separation.

anti-1-[4-(2-Carboxy-6-hydroxybenzoyl)-3,5-dihydroxybenzoyl-oxy]-2-(4-hydroxybenzamido)indane To a solution of the above white solids (180 mg, 0.24 mmol) in THF (60 mL) was added 60 drops of conc. HCl. The reaction mixture was stirred at rt for 24 h, and then chromatographed (silica gel, EtOAc:Hexane/4:1 containing 0.5% HOAc) to provide the title compound as a yellow solid (110 mg, 65% from aldehyde); mp 153°–156° C.

What is claimed is:

1. A compound selected from anti-3 -[4-(2-Carboxy-6-hydroxybenzoyl)-3,5-dihydroxybenzoyloxy]-2 (4-hydroxybenzamido)-8-methyl-8-azabicyclo[3.2.1]octane;

syn-3-[4-(2-Carboxy-6-hydroxybenzoyl)-3,5-dihydroxybenzoyl]-2(4-hydroxybenzamido)-8-methyl-8-azabicyclo[3.2.1]octane;

anti-2-(4-Hydroxybenzamido)-3-[4-(2-methoxycarbonyl-6-hydroxybenzoyl)-3,5-dihydroxybenzoyloxy]-8-methyl-8-azabicyclo[3.2.1]octane;

syn-2-[4-(2-Methoxycarbonyl-6-hydroxybenzoyl)-3,5-dihydroxybenzoyloxy]-3-(4-hydroxybenzamido)bicyclo[2.2.1]heptane;

syn-2-[4-(2-Carboxy-6-hydroxybenzoyl)-3,5-dihydroxybenzoyloxy]-3-(4-hydroxybenzamido)bicyclo[2.2.1]heptane;

anti-2-[4-(2-Carboxy-6-hydroxybenzoyl)-3,5- dihydroxybenzoyloxy]-3-(4-hydroxybenzamido)bicyclo[2.2.1]heptane;

anti-2-[4-(2-Methoxycarbonyl-6-hydroxybenzoyl)-3,5-dihydroxybenzoyloxy]-3-(4-hydroxybenzamido)bicyclo[2.2.1]heptane;

7-[4-(2-Methoxycarbonyl-6-hydroxybenzoyl)-3,5-dihydroxybenzoyloxy]-2-(hydroxybenzamido)bicyclo[2.2.1]heptane;

7-[4-(2-Carboxy-6-hydroxybenzoyl)-3,5-dihydroxybenzoyloxy]-2-(hydroxybenzamido)bicyclo[2.2.1]heptane;

syn-4-[4-(2-Carboxy-6-hydroxybenzoyl)-3,5-dihydroxybenzoyloxy]-3-(4-hydroxybenzoylamino)-1-azabicyclo[3.2.2]nonane;

anti-4-[4-(2-Carboxy-6-hydroxybenzoyl)-3,5-dihydroxybenzoyloxy]-3-(4-hydroxybenzoylamino)-1-azabicyclo[3.2.2]nonane;

anti-4-[4-(2-Methoxycarbonyl-6-hydroxybenzoyl)-3,5-dihydroxybenzoyloxy]-3-(4-hydroxybenzamido)-1-azabicyclo[3.2.2]nonane;

anti-1-(4-Hydroxybenzamido)-2-[3,5-dihydroxy-4-(2-carboxy-6-hydroxybenzoyl)benzoyloxy]indane;

syn-1-(4-Hydroxybenzamido)-2-[3,5-dihydroxy-4-(2-carboxy-6-hydroxybenzoyl)benzoyloxy]indane; and anti-1-(4-Hydroxybenzamido)-2-[3,5-dihydroxy-4-(2-hydroxy-6-methoxycarbonylbenzoyl)benzoyloxy]indane.

2. A compound selected from anti-1-[4-(2-Carboxy-6-hydroxybenzoyl)-3,5-dihydroxybenzyloxy]-2-(4-hydroxybenzamido)indane;

anti-2-[4-(2-Carboxy-6-hydroxybenzoyl)-3,5-dihydroxybenzoyloxy]-3-(4-hydroxybenzamido)bicyclo[2.2.1]-1,7,7-trimethylheptane;

8-exo-[4-(2-Carboxy-6-hydroxybenzoyl)-3,5-dihydroxybenzoyloxy]-9-endo-(4-hydroxybenzamido)tricyclo[5.2.1.0 (2.6)]decane;

8-endo-[4-(2-Carboxy-6-hydroxybenzoyl)-3,5-dihydroxybenzoyloxy]-9-endo-(4-hydroxybenzamido)tricyclo[5.2.1.0 (2.6)]decane;

(+)-anti-1-(4-Hydroxybenzamido)-2-[3,5-dihydroxy-4-(2-carboxy-6-hydroxybenzoyl)benzoyloxy]indane; and (−)-anti-1-(4-Hydroxybenzamido)-2-[3,5-dihydroxy-4-(2-carboxy-6-hydroxybenzoyl)benzoyloxy]indane.

3. A pharmaceutical composition useful for producing a therapeutic effect that comprises a pharmaceutically acceptable carrier and a compound of claim 1.

4. A method for producing PKC inhibition in mammals which comprises administering to a subject an effective amount of a compound of claim 1.

5. A method of treating cardiovascular, metabolic, nervous system, viral infectious, fungal infectious or neoplastic diseases that comprises administering to subject affected by any such diseases an effective amount of a compound of claim 1.

6. A pharmaceutical composition useful for producing a therapeutic effect that comprises a pharmaceutically acceptable carrier and a compound of claim 2.

7. A method for producing PKC inhibition in mammals which comprises administering to a subject an effective amount of a compound of claim 2.

8. A method of treating cardiovascular, metabolic, nervous system, viral infectious, fungal infectious or neoplastic diseases that comprises administering to subject affected by any such diseases an effective amount of a compound of claim 2.

* * * * *